US008168160B2

(12) United States Patent
Gawaz et al.

(10) Patent No.: US 8,168,160 B2

(45) Date of Patent: May 1, 2012

(54) ANTI-INFLAMMATORY FUSION PROTEIN

(75) Inventors: Meinrad Gawaz, Tubingen (DE); Karin Daub, Penzberg (DE)

(73) Assignee: Eberhard-Karls-Universität Tübingen (DE)

( * ) Notice: Subject to any disclaimer, the term of this patent is extended or adjusted under 35 U.S.C. 154(b) by 392 days.

(21) Appl. No.: 12/272,670

(22) Filed: Nov. 17, 2008

(65) Prior Publication Data

US 2009/0162285 A1 Jun. 25, 2009

(30) Foreign Application Priority Data

May 17, 2006 (DE) ......................... 10 2006 024 113
Jul. 13, 2006 (DE) ......................... 10 2006 033 394

(51) Int. Cl.
*A61K 49/00* (2006.01)
*A61K 38/00* (2006.01)
*A61P 9/00* (2006.01)

(52) U.S. Cl. ....................................... 424/9.1; 514/16.4

(58) Field of Classification Search ........................ None
See application file for complete search history.

(56) References Cited

FOREIGN PATENT DOCUMENTS

EP 1046652 10/2000

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Bitonti, et al., "Pulmonary delivery of an erythropoietin Fc fusion in non-human primates through an immunoglobulin transport pathway", *PNAS*, vol. 101, 2004, pp. 9763-9768.
Gough, et al., "The use of human CD68 transcriptional regulatory sequences to direct high-level expression of class A scavenger receptor in macrophages in vitro and in vivo", *Immunology 103*, 2001, pp. 351-361.
Langer, et al., "Adherent platelets recruit and induce differentiation of murine embryonic endothelial progenitor cells to mature endothelial cells in vitro", *Circ. Res. 98*(2): e2-10, 2006 (electronic 2005).
Ramprasad, et al., "Cell surface of mouse macrosialin and human CD68 and their role as macrophage receptors for oxidized low density lipoprotein",*PNAS*, vol. 93, 1996, pp. 14833-14838.
Siegel-Axel, et al., "Specific inhibition of foam cell formation by a soluble CD68-Fc fusion protein", *Tissue Engineering*, vol. 13, No. 4, Apr. 2007, abstract No. P68, p. 914.
Siegel-Axel, et al., "The soluble immunoadhesin CD68-Fc: an innovative anti-atherosclerotic strategy for the specific inhibition of foam cell formation", *Journal of Clinical Lipidology*, vol. 1, No. 5, Oct. 2007, abstract No. 343, p. 476.
International Search Report from PCT/2007003984, dated Nov. 5, 2007.
English language translation of the International Preliminary Report on Patentability and Written Opinion from PCT Application No. PCT/EP2007/003984, 10 pages, (mailed May 14, 2009).

* cited by examiner

*Primary Examiner* — Marcela M Cordero Garcia
(74) *Attorney, Agent, or Firm* — Klarquist Sparkman, LLP.

(57) ABSTRACT

The present invention relates to a fusion protein comprising therapeutic and diagnostic potential against chronic vascular diseases, such as atherosclerosis, a nucleic acid molecule encoding said fusion protein, a pharmaceutical and diagnostic composition which comprises the fusion protein or the nucleic acid molecule, the use of the fusion protein or the nucleic acid molecule for the production of a pharmaceutical and diagnostic composition, a method for the diagnosis of acute or chronic vascular diseases, and a method for the production of a fusion protein.

6 Claims, 7 Drawing Sheets

SEQUENCE LISTING

```
<160> NUMBER OF SEQ ID NOS: 12

<210> SEQ ID NO 1
<211> LENGTH: 298
<212> TYPE: PRT
<213> ORGANISM: Homo sapiens

<400> SEQUENCE: 1

Asn Asp Cys Pro His Lys Lys Ser Ala Thr Leu Leu Pro Ser Phe Thr
1               5                   10                  15

Val Thr Pro Thr Val Thr Glu Ser Thr Gly Thr Thr Ser His Arg Thr
            20                  25                  30

Thr Lys Ser His Lys Thr Thr Thr His Arg Thr Thr Thr Thr Gly Thr
        35                  40                  45

Thr Ser His Gly Pro Thr Thr Ala Thr His Asn Pro Thr Thr Thr Ser
    50                  55                  60

His Gly Asn Val Thr Val His Pro Thr Ser Asn Ser Thr Ala Thr Ser
65                  70                  75                  80

Gln Gly Pro Ser Thr Ala Thr His Ser Pro Ala Thr Thr Ser His Gly
                85                  90                  95

Asn Ala Thr Val His Pro Thr Ser Asn Ser Thr Ala Thr Ser Pro Gly
            100                 105                 110

Phe Thr Ser Ser Ala His Pro Glu Pro Pro Pro Pro Ser Pro Ser Pro
        115                 120                 125

Ser Pro Thr Ser Lys Glu Thr Ile Gly Asp Tyr Thr Trp Thr Asn Gly
    130                 135                 140

Ser Gln Pro Cys Val His Leu Gln Ala Gln Ile Gln Ile Arg Val Met
145                 150                 155                 160

Tyr Thr Thr Gln Gly Gly Gly Glu Ala Trp Gly Ile Ser Val Leu Asn
                165                 170                 175

Pro Asn Lys Thr Lys Val Gln Gly Ser Cys Glu Gly Ala His Pro His
            180                 185                 190

Leu Leu Leu Ser Phe Pro Tyr Gly His Leu Ser Phe Gly Phe Met Gln
        195                 200                 205

Asp Leu Gln Gln Lys Val Val Tyr Leu Ser Tyr Met Ala Val Glu Tyr
    210                 215                 220

Asn Val Ser Phe Pro His Ala Ala Gln Trp Thr Phe Ser Ala Gln Asn
225                 230                 235                 240

Ala Ser Leu Arg Asp Leu Gln Ala Pro Leu Gly Gln Ser Phe Ser Cys
                245                 250                 255

Ser Asn Ser Ser Ile Ile Leu Ser Pro Ala Val His Leu Asp Leu Leu
            260                 265                 270

Ser Leu Arg Leu Gln Ala Ala Gln Leu Pro His Thr Gly Val Phe Gly
        275                 280                 285
```

```
Gln Ser Phe Ser Cys Pro Ser Asp Arg Ser
    290                 295


<210> SEQ ID NO 2
<211> LENGTH: 894
<212> TYPE: DNA
<213> ORGANISM: Homo sapiens

<400> SEQUENCE: 2

aatgactgtc ctcacaaaaa atcagctact ttgctgccat ccttcacggt gacacccacg     60

gttacagaga gcactggaac aaccagccac aggactacca agagccacaa aaccaccact    120

cacaggacaa ccaccacagg caccaccagc cacggaccca cgactgccac tcacaacccc    180

accaccacca gccatggaaa cgtcacagtt catccaacaa gcaatagcac tgccaccagc    240

cagggaccct caactgccac tcacagtcct gccaccacta gtcatggaaa tgccacggtt    300

catccaacaa gcaacagcac tgccaccagc ccaggattca ccagttctgc ccacccagaa    360

ccacctccac cctctccgag tcctagccca acctccaagg agaccattgg agactacacg    420

tggaccaatg gttcccagcc ctgtgtccac ctccaagccc agattcagat tcgagtcatg    480

tacacaaccc agggtggagg agaggcctgg ggcatctctg tactgaaccc caacaaaacc    540

aaggtccagg gaagctgtga gggtgcccat ccccacctgc ttctctcatt cccctatgga    600

cacctcagct ttggattcat gcaggacctc cagcagaagg ttgtctacct gagctacatg    660

gcggtggagt acaatgtgtc cttcccccac gcagcacagt ggacattctc ggctcagaat    720

gcatcccttc gagatctcca agcacccctg ggcagagct tcagttgcag caactcgagc    780

atcattcttt caccagctgt ccacctcgac ctgctctccc tgaggctcca ggctgctcag    840

ctgccccaca caggggtctt tgggcaaagt ttctcctgcc ccagtgaccg gtcc          894


<210> SEQ ID NO 3
<211> LENGTH: 894
<212> TYPE: DNA
<213> ORGANISM: Homo sapiens

<400> SEQUENCE: 3

aatgactgtc ctcacaaaaa atcagctact ttgctgccat ccttcacggt gacacccacg     60

gttacagaga gcactggaac aaccagccac aggactacca agagccacaa aaccaccact    120

cacaggacaa ccaccacagg caccaccagc cacggaccca cgactgccac tcacaacccc    180

accaccacca gccatggaaa cgtcacagtt catccaacaa gcaatagcac tgccaccagc    240

cagggaccct caactgccac tcacagtcct gccaccacta gtcatggaaa tgccacggtt    300

catccaacaa gcaacagcac tgccaccagc ccaggattca ccagttctgc ccacccagaa    360

ccacctccac cctctccgag tcctagccca acctccaagg agaccattgg agactacacg    420

tggaccaatg gttcccagcc ctgtgtccac ctccaagccc agattcagat tcgagtcatg    480

tacacaaccc agggtggagg agaggcctgg ggcatctctg tactgaaccc caacaaaacc    540

aaggtccagg gaagctgtga gggtgcccat ccccacctgc ttctctcatt cccctatgga    600

cacctcagct ttggattcat gcaggacctc cagcagaagg ttgtctacct gagctacatg    660

gcggtggagt acaatgtgtc cttcccccac gcagcaaagt ggacattctc ggctcagaat    720

gcatcccttc gagatctcca agcacccctg ggcagagct tcagttgcag caactcgagc    780

atcattcttt caccagctgt ccacctcgac ctgctctccc tgaggctcca ggctgctcag    840

ctgccccaca caggggtctt tgggcaaagt ttctcctgcc ccagtgaccg gtcc          894
```

<210> SEQ ID NO 4
<211> LENGTH: 232
<212> TYPE: PRT
<213> ORGANISM: Artificial sequence
<220> FEATURE:
<223> OTHER INFORMATION: Recombinant Fc domain polypeptide

<400> SEQUENCE: 4

```
Glu Ser Lys Ser Cys Asp Lys Thr His Thr Cys Pro Pro Cys Pro Ala
1               5                   10                  15

Pro Glu Ala Ala Ala Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 5
<211> LENGTH: 699
<212> TYPE: DNA
<213> ORGANISM: Artificial sequence
<220> FEATURE:
<223> OTHER INFORMATION: Nucleic acids encoding recombinant Fc domain polypeptide

<400> SEQUENCE: 5

```
gagtctaagt cctgtgataa gactcatacc tgcccccct gcccagcacc cgaggcagca      60

gccgcccct cagtgtttct cttccctcca aaacccaagg ataccctgat gatcagccgt     120

acacctgagg tcacctgcgt agtcgtcgat gtgtctcacg aggacccgga ggtgaagttt     180

aattggtatg tggacggggt agaagtgcat aatgccaaga ctaaacctcg agaggaacaa     240

tataactcca cctataggt ggtcagcgtt ctcacggtcc ttcaccagga ctggttgaat     300

ggaaaggaat acaagtgtaa ggtgagcaac aaagccctgc ccgcttccat agaaaagaca     360

atctccaaag ctaaagggca gccacgggaa cctcaggtgt acaccctgcc gcctagcaga     420

gatgagctca caaagaacca ggtgtctctg acatgcttgg tgaagggttt ctatccttcg     480
```

gacattgccg ttgagtggga aagtaacggc cagcctgaga ataactacaa gaccacacca 540
cccgttcttg actctgatgg gagtttcttt ttgtacagta agttaactgt cgacaaatca 600
cgctggcagc aaggaaatgt tttctcttgt tccgtgatgc acgaggcact gcacaaccat 660
tacactcaga aatccctgag cctatcacca ggcaaataa 699

<210> SEQ ID NO 6
<211> LENGTH: 533
<212> TYPE: PRT
<213> ORGANISM: Artificial sequence
<220> FEATURE:
<223> OTHER INFORMATION: Recombinant CD68-Fc fusion protein

<400> SEQUENCE: 6

Asn Asp Cys Pro His Lys Lys Ser Ala Thr Leu Leu Pro Ser Phe Thr
1 5 10 15

Val Thr Pro Thr Val Thr Glu Ser Thr Gly Thr Thr Ser His Arg Thr
20 25 30

Thr Lys Ser His Lys Thr Thr Thr His Arg Thr Thr Thr Thr Gly Thr
35 40 45

Thr Ser His Gly Pro Thr Thr Ala Thr His Asn Pro Thr Thr Thr Ser
50 55 60

His Gly Asn Val Thr Val His Pro Thr Ser Asn Ser Thr Ala Thr Ser
65 70 75 80

Gln Gly Pro Ser Thr Ala Thr His Ser Pro Ala Thr Thr Ser His Gly
85 90 95

Asn Ala Thr Val His Pro Thr Ser Asn Ser Thr Ala Thr Ser Pro Gly
100 105 110

Phe Thr Ser Ser Ala His Pro Glu Pro Pro Pro Pro Ser Pro Ser Pro
115 120 125

Ser Pro Thr Ser Lys Glu Thr Ile Gly Asp Tyr Thr Trp Thr Asn Gly
130 135 140

Ser Gln Pro Cys Val His Leu Gln Ala Gln Ile Gln Ile Arg Val Met
145 150 155 160

Tyr Thr Thr Gln Gly Gly Gly Glu Ala Trp Gly Ile Ser Val Leu Asn
165 170 175

Pro Asn Lys Thr Lys Val Gln Gly Ser Cys Glu Gly Ala His Pro His
180 185 190

Leu Leu Leu Ser Phe Pro Tyr Gly His Leu Ser Phe Gly Phe Met Gln
195 200 205

Asp Leu Gln Gln Lys Val Val Tyr Leu Ser Tyr Met Ala Val Glu Tyr
210 215 220

Asn Val Ser Phe Pro His Ala Ala Gln Trp Thr Phe Ser Ala Gln Asn
225 230 235 240

Ala Ser Leu Arg Asp Leu Gln Ala Pro Leu Gly Gln Ser Phe Ser Cys
245 250 255

Ser Asn Ser Ser Ile Ile Leu Ser Pro Ala Val His Leu Asp Leu Leu
260 265 270

Ser Leu Arg Leu Gln Ala Ala Gln Leu Pro His Thr Gly Val Phe Gly
275 280 285

Gln Ser Phe Ser Cys Pro Ser Asp Arg Ser Gly Gly Arg Glu Ser Lys
290 295 300

Ser Cys Asp Lys Thr His Thr Cys Pro Pro Cys Pro Ala Pro Glu Ala
305 310 315 320

Ala Ala Ala Pro Ser Val Phe Leu Phe Pro Pro Lys Pro Lys Asp Thr

```
                325                 330                 335

Leu Met Ile Ser Arg Thr Pro Glu Val Thr Cys Val Val Val Asp Val
            340                 345                 350

Ser His Glu Asp Pro Glu Val Lys Phe Asn Trp Tyr Val Asp Gly Val
        355                 360                 365

Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Pro Ala
                405                 410                 415

Ser Ile Glu Lys Thr Ile Ser Lys Ala Lys Gly Gln Pro Arg Glu Pro
            420                 425                 430

Gln Val Tyr Thr Leu Pro Pro Ser Arg Asp Glu Leu Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys
    530

<210> SEQ ID NO 7
<211> LENGTH: 1602
<212> TYPE: DNA
<213> ORGANISM: Artificial sequence
<220> FEATURE:
<223> OTHER INFORMATION: Nucleic acid sequence encoding recombinant
      CD68-Fc fusion protein

<400> SEQUENCE: 7

aatgactgtc ctcacaaaaa atcagctact ttgctgccat ccttcacggt gacacccacg      60

gttacagaga gcactggaac aaccagccac aggactacca agagccacaa aaccaccact     120

cacaggacaa ccaccacagg caccaccagc cacggaccca cgactgccac tcacaacccc     180

accaccacca gccatggaaa cgtcacagtt catccaacaa gcaatagcac tgccaccagc     240

cagggaccct caactgccac tcacagtcct gccaccacta gtcatggaaa tgccacggtt     300

catccaacaa gcaacagcac tgccaccagc ccaggattca ccagttctgc ccacccagaa     360

ccacctccac cctctccgag tcctagccca acctccaagg agaccattgg agactacacg     420

tggaccaatg gttcccagcc ctgtgtccac ctccaagccc agattcagat tcgagtcatg     480

tacacaaccc agggtggagg agaggcctgg ggcatctctg tactgaaccc caacaaaacc     540

aaggtccagg gaagctgtga gggtgcccat ccccacctgc ttctctcatt cccctatgga     600

cacctcagct ttggattcat gcaggacctc cagcagaagg ttgtctacct gagctacatg     660

gcggtggagt acaatgtgtc cttcccccac gcagcacagt ggacattctc ggctcagaat     720

gcatcccttc gagatctcca agcacccctg ggcagagct  tcagttgcag caactcgagc     780

atcattcttt caccagctgt ccacctcgac ctgctctccc tgaggctcca ggctgctcag     840
```

```
ctgccccaca caggggtctt tgggcaaagt ttctcctgcc ccagtgaccg gtccggcggc    900

cgcgagtcta agtcctgtga taagactcat acctgccccc cctgcccagc acccgaggca    960

gcagccgccc cctcagtgtt tctcttccct ccaaaaccca aggataccct gatgatcagc   1020

cgtacacctg aggtcacctg cgtagtcgtc gatgtgtctc acgaggaccc ggaggtgaag   1080

tttaattggt atgtggacgg ggtagaagtg cataatgcca agactaaacc tcgagaggaa   1140

caatataact ccacctatag ggtggtcagc gttctcacgg tccttcacca ggactggttg   1200

aatggaaagg aatacaagtg taaggtgagc aacaaagccc tgcccgcttc catagaaaag   1260

acaatctcca aagctaaagg gcagccacgg gaacctcagg tgtacaccct gccgcctagc   1320

agagatgagc tcacaaagaa ccaggtgtct ctgacatgct tggtgaaggg tttctatcct   1380

tcggacattg ccgttgagtg ggaaagtaac ggccagcctg agaataacta caagaccaca   1440

ccacccgttc ttgactctga tgggagtttc tttttgtaca gtaagttaac tgtcgacaaa   1500

tcacgctggc agcaaggaaa tgttttctct tgttccgtga tgcacgaggc actgcacaac   1560

cattacactc agaaatccct gagcctatca ccaggcaaat aa                      1602
```

```
<210> SEQ ID NO 8
<211> LENGTH: 1602
<212> TYPE: DNA
<213> ORGANISM: Artificial sequence
<220> FEATURE:
<223> OTHER INFORMATION: Nucleic acid sequence encoding recombinant
      CD68-Fc fusion protein

<400> SEQUENCE: 8
```

```
aatgactgtc ctcacaaaaa atcagctact ttgctgccat ccttcacggt gacacccacg     60

gttacagaga gcactggaac aaccagccac aggactacca agagccacaa aaccaccact    120

cacaggacaa ccaccacagg caccaccagc cacggaccca cgactgccac tcacaacccc    180

accaccacca gccatggaaa cgtcacagtt catccaacaa gcaatagcac tgccaccagc    240

cagggaccct caactgccac tcacagtcct gccaccacta gtcatggaaa tgccacggtt    300

catccaacaa gcaacagcac tgccaccagc ccaggattca ccagttctgc ccacccagaa    360

ccacctccac cctctccgag tcctagccca acctccaagg agaccattgg agactacacg    420

tggaccaatg gttcccagcc ctgtgtccac ctccaagccc agattcagat tcgagtcatg    480

tacacaaccc agggtggagg agaggcctgg ggcatctctg tactgaaccc caacaaaacc    540

aaggtccagg gaagctgtga gggtgcccat ccccacctgc ttctctcatt cccctatgga    600

cacctcagct ttggattcat gcaggacctc cagcagaagg ttgtctacct gagctacatg    660

gcggtggagt acaatgtgtc cttcccccac gcagcaaagt ggacattctc ggctcagaat    720

gcatcccttc gagatctcca agcacccctg ggcagagct tcagttgcag caactcgagc     780

atcattcttt caccagctgt ccacctcgac ctgctctccc tgaggctcca ggctgctcag    840

ctgccccaca caggggtctt tgggcaaagt ttctcctgcc ccagtgaccg gtccggcggc    900

cgcgagtcta agtcctgtga taagactcat acctgccccc cctgcccagc acccgaggca    960

gcagccgccc cctcagtgtt tctcttccct ccaaaaccca aggataccct gatgatcagc   1020

cgtacacctg aggtcacctg cgtagtcgtc gatgtgtctc acgaggaccc ggaggtgaag   1080

tttaattggt atgtggacgg ggtagaagtg cataatgcca agactaaacc tcgagaggaa   1140

caatataact ccacctatag ggtggtcagc gttctcacgg tccttcacca ggactggttg   1200

aatggaaagg aatacaagtg taaggtgagc aacaaagccc tgcccgcttc catagaaaag   1260

acaatctcca aagctaaagg gcagccacgg gaacctcagg tgtacaccct gccgcctagc   1320
```

```
agagatgagc tcacaaagaa ccaggtgtct ctgacatgct tggtgaaggg tttctatcct   1380

tcggacattg ccgttgagtg ggaaagtaac ggccagcctg agaataacta caagaccaca   1440

ccacccgttc ttgactctga tgggagtttc tttttgtaca gtaagttaac tgtcgacaaa   1500

tcacgctggc agcaaggaaa tgttttctct tgttccgtga tgcacgaggc actgcacaac   1560

cattacactc agaaatccct gagcctatca ccaggcaaat aa                      1602
```

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide linker.

<400> SEQUENCE: 9

```
Leu Leu Gly Gly
1
```

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide linker.

<400> SEQUENCE: 10

```
Ala Ala Ala Ala
1
```

<210> SEQ ID NO 11
<211> LENGTH: 1704
<212> TYPE: DNA
<213> ORGANISM: Artificial Sequence
<220> FEATURE:
<223> OTHER INFORMATION: Nucleic acid sequence encoding recombinant CD68-Fc fusion protein

<400> SEQUENCE: 11

```
atggagacag acacactcct gctatgggta ctgctgctct gggttccagg ttccactggt     60

gacgcggccc agccggccag gcgcgcgcgc cgtacgaagc ttaatgactg tcctcacaaa    120

aaatcagcta ctttgctgcc atccttcacg gtgacaccca cggttacaga gagcactgga    180

acaaccagcc acaggactac caagagccac aaaaccacca ctcacaggac aaccaccaca    240

ggcaccacca gccacggacc cacgactgcc actcacaacc ccaccaccac cagccatgga    300

aacgtcacag ttcatccaac aagcaatagc actgccacca gccagggacc ctcaactgcc    360

actcacagtc ctgccaccac tagtcatgga aatgccacgg ttcatccaac aagcaacagc    420

actgccacca gcccaggatt caccagttct gcccacccag aaccacctcc accctctccg    480

agtcctagcc caacctccaa ggagaccatt ggagactaca cgtggaccaa tggttcccag    540

ccctgtgtcc acctccaagc ccagattcag attcgagtca tgtacacaac ccagggtgga    600

ggagaggcct ggggcatctc tgtactgaac cccaacaaaa ccaaggtcca gggaagctgt    660

gagggtgccc atccccacct gcttctctca ttcccctatg gacacctcag ctttggattc    720

atgcaggacc tccagcagaa ggttgtctac ctgagctaca tggcggtgga gtacaatgtg    780

tccttccccc acgcagcaca gtggacattc tcggctcaga atgcatccct tcgagatctc    840

caagcacccc tggggcagag cttcagttgc agcaactcga gcatcattct ttcaccagct    900

gtccacctcg acctgctctc cctgaggctc caggctgctc agctgcccca cacaggggtc    960
```

```
tttgggcaaa gtttctcctg ccccagtgac cggtccggcg gccgcgagtc taagtcctgt   1020

gataagactc atacctgccc cccctgccca gcacccgagg cagcagccgc cccctcagtg   1080

tttctcttcc ctccaaaacc caaggatacc ctgatgatca gccgtacacc tgaggtcacc   1140

tgcgtagtcg tcgatgtgtc tcacgaggac ccggaggtga agtttaattg gtatgtggac   1200

ggggtagaag tgcataatgc caagactaaa cctcgagagg aacaatataa ctccacctat   1260

agggtggtca gcgttctcac ggtccttcac caggactggt tgaatggaaa ggaatacaag   1320

tgtaaggtga gcaacaaagc cctgcccgct tccatagaaa agacaatctc caaagctaaa   1380

gggcagccac gggaacctca ggtgtacacc ctgccgccta gcagagatga gctcacaaag   1440

aaccaggtgt ctctgacatg cttggtgaag ggtttctatc cttcggacat tgccgttgag   1500

tgggaaagta acggccagcc tgagaataac tacaagacca caccacccgt tcttgactct   1560

gatgggagtt tctttttgta cagtaagtta actgtcgaca aatcacgctg gcagcaagga   1620

aatgttttct cttgttccgt gatgcacgag gcactgcaca accattacac tcagaaatcc   1680

ctgagcctat caccaggcaa ataa                                          1704
```

<210> SEQ ID NO 12
<211> LENGTH: 567
<212> TYPE: PRT
<213> ORGANISM: Artificial Sequence
<220> FEATURE:
<223> OTHER INFORMATION: Recombinant CD68-Fc fusion protein

<400> SEQUENCE: 12

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Asn Asp Cys Pro His Lys Lys Ser Ala Thr Leu Leu Pro Ser
        35                  40                  45

Phe Thr Val Thr Pro Thr Val Thr Glu Ser Thr Gly Thr Thr Ser His
    50                  55                  60

Arg Thr Thr Lys Ser His Lys Thr Thr Thr His Arg Thr Thr Thr Thr
65                  70                  75                  80

Gly Thr Thr Ser His Gly Pro Thr Thr Ala Thr His Asn Pro Thr Thr
                85                  90                  95

Thr Ser His Gly Asn Val Thr Val His Pro Thr Ser Asn Ser Thr Ala
            100                 105                 110

Thr Ser Gln Gly Pro Ser Thr Ala Thr His Ser Pro Ala Thr Thr Ser
        115                 120                 125

His Gly Asn Ala Thr Val His Pro Thr Ser Asn Ser Thr Ala Thr Ser
    130                 135                 140

Pro Gly Phe Thr Ser Ser Ala His Pro Glu Pro Pro Pro Pro Ser Pro
145                 150                 155                 160

Ser Pro Ser Pro Thr Ser Lys Glu Thr Ile Gly Asp Tyr Thr Trp Thr
                165                 170                 175

Asn Gly Ser Gln Pro Cys Val His Leu Gln Ala Gln Ile Gln Ile Arg
            180                 185                 190

Val Met Tyr Thr Thr Gln Gly Gly Gly Glu Ala Trp Gly Ile Ser Val
        195                 200                 205

Leu Asn Pro Asn Lys Thr Lys Val Gln Gly Ser Cys Glu Gly Ala His
    210                 215                 220

Pro His Leu Leu Leu Ser Phe Pro Tyr Gly His Leu Ser Phe Gly Phe
225                 230                 235                 240
```

-continued

```
Met Gln Asp Leu Gln Gln Lys Val Val Tyr Leu Ser Tyr Met Ala Val
                245                 250                 255

Glu Tyr Asn Val Ser Phe Pro His Ala Ala Gln Trp Thr Phe Ser Ala
            260                 265                 270

Gln Asn Ala Ser Leu Arg Asp Leu Gln Ala Pro Leu Gly Gln Ser Phe
        275                 280                 285

Ser Cys Ser Asn Ser Ser Ile Ile Leu Ser Pro Ala Val His Leu Asp
    290                 295                 300

Leu Leu Ser Leu Arg Leu Gln Ala Ala Gln Leu Pro His Thr Gly Val
305                 310                 315                 320

Phe Gly Gln Ser Phe Ser Cys Pro Ser Asp Arg Ser Gly Gly Arg Glu
                325                 330                 335

Ser Lys Ser Cys Asp Lys Thr His Thr Cys Pro Pro Cys Pro Ala Pro
            340                 345                 350

Glu Ala Ala Ala Ala Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445

Pro Ala Ser Ile Glu Lys Thr Ile Ser Lys Ala Lys Gly Gln Pro Arg
    450                 455                 460

Glu Pro Gln Val Tyr Thr Leu Pro Pro Ser Arg Asp Glu Leu Thr Lys
465                 470                 475                 480

Asn Gln Val Ser Leu Thr Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560

Leu Ser Leu Ser Pro Gly Lys
                565
```

ANTI-INFLAMMATORY FUSION PROTEIN

CROSS-REFERENCES TO RELATES APPLICATIONS

This application is a continuation application of copending international patent application PCT/EP2007/003984 filed on May 5, 2007 and designating the United States, which was not published under PCT Article 21(2) in English, and claims priority of German patent application DE 10 2006 024 113.4 filed on May 17, 2006, and of German patent application DE 10 2006 033 394.2 filed on Jul. 13, 2006, which are incorporated herein by reference.

BACKGROUND OF THE INVENTION

1. Field of the Invention

The present invention relates to a fusion protein comprising therapeutic and diagnostic capacity against chronic vascular diseases, such as atherosclerosis, a nucleic acid molecule encoding said fusion protein, a pharmaceutical and diagnostic composition which comprises said fusion protein or nucleic acid molecule, a use of said fusion protein or nucleic acid molecule for the production of a pharmaceutical or diagnostic composition, a method for the diagnosis of acute or chronic vascular diseases, as well as a method for the production of said fusion protein.

2. Related Prior Art

Atherosclerosis is a highly complex active pathological process, in the center of which is an inflammatory reaction in the walls of the sanguiferous vessels of an affected individuum. The development of atherosclerosis, the so-called atherogenesis, can be subdivided into several phases.

The early phase of atherogenesis is characterized by a so-called endothelial dysfunction. A number of different risk factors such as smoking, overweight, physical inactivity, hyperlipidemia and type II diabetes as well as other so far not identified factors cause a damage of the endothelium. The permeability of the endothelium for lipoproteins and other circulating substances in the plasma is hereby increased. As a result endothelial cells are activated and increase the expression of so-called adhesion molecules on their cell surface. Among them in particular so-called selectins initially mediate a temporary contact of specific blood cells such as monocytes and T-lymphocytes with the endothelium. Another group of adhesion molecules, the so-called cellular adhesion molecules (CAMs), causes a tight attachment of these cells to the vascular wall. In particular at branchings of the vessels—the locations where atherosclerotic lesions very often develop—mechanical forces play an additional role. Increased shearing forces can reduce the production of endothelial nitrogen (NO). NO acts as a vasodilator and has anti-inflammatory properties. Furthermore, increased shearing forces result in an increased production of adhesion molecules with the above-described results.

In the further course in particular monocytes and to a lesser extent T-lymphocytes infiltrate the subintimal room. This infiltration is mediated through another group of molecules to which e.g. the chemokine monocyte chemoattractant protein 1 (MCP-1) belongs. This results in a differentiation of the monocytes into macrophages in the subintimal room.

Moreover, in the damaged endothelium an oxidation of lipoproteins of low density (LDL) occurs and as a result oxLDL is formed. oxLDL is secreted into the subintimal room where it loaded on the macrophages resulting from the monocytes. As a result of this loading with oxLDL these macrophages are transformed into so-called foam cells, the characteristic cells of the atherosclerotic plaques which contain as further components inter alia T-lymphocytes and smooth muscle cells immigrated from the media.

Such an atherosclerotic plaque deposits on the arterial walls and is covered by a stabilizing fibrous cap consisting of smooth muscle cells and extracellular matrix. The atherosclerotic plaque is now in the center of an inflammatory reaction which results in a production of different inflammation mediators such as cytokines, chemokines, proteases etc. This can result in a necrosis of tissue in which neighborhood calcium carbonates are deposited. Thereby the vascular lumen can be narrowed up to the complete closure with the result of disturbed blood flow.

If the smooth muscle cells reduce the formation of extracellular matrix and the latter is increasingly degraded by degrading enzymes, the fibrous cap is thinned out and the atherosclerotic plaque is destabilized. The plaque can dehisce whereby the thrombogenic lipid core and collagen in the vascular wall is exposed. This results in an activation of the haemostasis system which in turn results in an occluding and non-occluding thrombus formation, i.e. in the activation of the coagulation cascade, in the center of which is the so-called tissue factor (TF). The rupture of the plaque with the formation of a thrombus becomes clinically manifest as instable Angina pectoris or acute myocard infarction.

At present the atherosclerosis is normally treated by the application of lipid lowering drugs or statines, respectively. These are a group of active substances which finally inhibit the endogenic synthesis of cholesterol. Substances which belong to the statines are inter alia Atorvastatin, Cerivastatin, Fluvastatin, Lovastatin (Mevinolin), Mevastatin (Compactin), Pravastatin and Simvastatin. These substances have influence on the lipid metabolism in different ways, e.g. by a competitive inhibition of the key enzyme of the cholesterol synthesis, the 3-hydroxy-3-methylglutaryl-coenzyme-A-reductase, by lowering the biosynthesis of cholesterol in the liver, by amplification of the LDL receptors on the liver cell, and by modification of lipoprotein composition. Statines have a large influence on the composition of the serum lipids and cause inter alia a slight increase of the concentration of so-called "high density lipoproteins" (HDL) and a strong decrease of the LDL concentration. Finally, by the effect of the statines a fewer amount of fats circulate in the blood, so that the atherosclerotic plaques store less fat and thereby the risk of a thrombosis and the endangerings resulting therefrom decrease.

Even though a number of other positive characteristics are attributed to the statines, the latter came under criticism for a noticeable accumulation of rare, however fatal side effects on muscles and kidneys in connection with their intake. For this reason in particular the active substance Cerivastatin (e.g. Lipobay®, Zenas®) has been removed from the German market in August 2001.

SUMMARY OF THE INVENTION

Against this background the object underlying the invention is to provide a new substance which comprises therapeutic and diagnostic potential in relation with the treatment and diagnosis of acute or chronic vascular diseases, such as atherosclerosis or atherosclerotic plaques, and by which the before-mentioned disadvantages of the known lipid lowering drugs can be reduced or avoided to a large extent.

This object is achieved by providing a fusion protein which comprises (a) a first polypeptide which specifically binds to modified LDL, and (b) a second polypeptide which mediates a dimerization.

According to the invention a fusion protein refers to a hybrid protein or an artificial protein, respectively, which can be produced in vitro but also in vivo by molecular biological methods known in the art. For this purpose preferably common expression vectors are used, which encode the fusion protein according to the invention. These expression vectors are introduced in an appropriate cell which consequently produces the fusion protein.

The first polypeptide is designed by choosing an appropriate amino acid sequence in such a manner that it takes a secondary or tertiary structure which selectively and highly affinely binds to modified low density lipoprotein (LDL). This is easy for a chemist familiar in the field of protein synthesis since the three-dimensional structure of modified LDL is known in the art. The second polypeptide is designed in view of its amino acid sequence in such a manner that it comprises a segment of a protein which is involved in the mediation of a dimerization of two separate proteins or protein subunits. Also this measure is easy for the skilled person since the microstructure including the amino acid sequences of peptidic dimeric structures of a large number of proteins are described in the art in detail. Known dimer-forming proteins which are known with regards to their sequence and structure comprise G-proteins, histones, interferon γ, interleukin-2-receptor, hsp90, tyrosine kinases, IgG molecules etc. Each of the domains of the mentioned proteins, which mediate the dimerization, can directly be used for the production of the fusion protein according to the invention. However, it can be favored to modify these domains by targeted mutagenesis or by adding specific amino acids to the C and/or N termini, resulting e.g. in a reduction of the immunologic effect of the fusion protein, to allow a better production of the fusion protein, however maintaining the dimerization function to a large extent.

According to the invention modified LDL refers to a low density lipoprotein which is chemically modified in such a manner that it corresponds to a variant which is produced in the damaged endothelium within the context of the atherogenesis. This applies to oxidized LDL (oxLDL), acetylated LDL (acLDL), enzymatically oxidized LDL (eLDL), and minimally modified LDL (mmLDL).

The object underlying the invention is herewith completely achieved. The inventors have realized that a fusion protein according to the invention after the application into a living being preferably accumulates exclusively at pre-damaged or atherosclerotically altered vascular areas, so that possible non-specific systemic side effects can be largely avoided. The fusion protein according to the invention absorbs the modified LDL due to the high affinity thereto, which is mediated by the first polypeptide segment. Even though also a monomer of the fusion protein is able to absorb modified LDL, by the dimerization of two fusion proteins according to the invention, which is mediated by the second polypeptide segment, the affinity to modified LDL is many times higher.

The complexation inactivates the modified LDL and the loading of macrophages and the subsequent transformation of these cells into foam cells is thereby avoided or largely reduced. As a result an intervention into the atherogenesis takes place in an early phase. The formation of atherosclerotic plaques and the above-mentioned fatal effects on the organism are remarkably inhibited and possibly even prevented. Another important advantage is that the complex of the fusion protein and the modified LDL is less immunogenic due to its complete human origin, and any inflammatory reactions in relation with the "removal" take place in an extremely mild fashion or are even absent.

It is thereby preferred if the first polypeptide is designed in such a manner that it binds to oxidized LDL (oxLDL).

This measure has the advantage that such a fusion protein is provided which binds and absorbs exactly that LDL variant which plays a decisive role for the transformation of macrophages into foam cells. With this further development according to the invention oxLDL as a key factor of the atherogenesis is weakened in its function or even eliminated in a targeted manner.

According to a further development of the invention the first polypeptide comprises the scavenger receptor CD68, preferably the extracellular domain of CD68 or a fragment or such a variant of the extracellular domain of CD68, which comprises the LDL binding function of CD68.

This measure has the advantage that as the first polypeptide such a polypeptide is provided which comprises a particular high and selective affinity to modified LDL, in particular to oxLDL. CD68 which is also designated as macrosialin or gp110, is a transmembrane glycoprotein which is highly expressed in monocytes or tissue macrophages. The amino acid sequence as well as the encoding nucleotide sequence are disclosed in the art; cf. the NCBI database accession Nos. AAB25811 or NP_001242 (amino acid sequence of the human variant), database accession No. NM_001251 or AAH15557 (nucleotide sequence of the mRNA of the human variant). The before-identified amino acid and nucleotide sequences are herewith incorporated into the present application by reference.

The human variant of CD68 is a protein having a size of 110 kD, which consists of 354 amino acids. CD68 belongs to the so-called scavenger receptors, since it can bind to modified LDL via its extracellular domain. CD68 is naturally expressed on the surface of monocytes, macrophages, neutrophil and basophil cells as well as large lymphocytes.

It is further preferred if the first polypeptide does not comprise the entire amino acid sequence of CD68 but the extracellular domain of CD68.

This measure has the particular advantage that peptide segments are omitted which are not required for the function of the fusion protein according to the invention. The fusion protein according to the invention is reduced in its size without losing its affinity to modified LDL. By this measure the solubility of the fusion protein according to the invention is remarkably increased. The inventors took advantage of the scientific discovery that the extracellular domain of CD68 is responsible and sufficient for the binding to modified LDL. The extracellular domain of CD68 of the human variant (NCBI accession No. AAH15557; Strausberg et al.) comprises about the amino acid residues of the positions 22 to 319 in the entire protein, which on the level of the mRNA correspond to the nucleotides at the positions 66 to 960. It goes without saying that a delimitation to exact one amino acid residual or one nucleotide is not possible by nature.

It shall be understood for a skilled person that for the realization of the function according to the invention the fusion protein does not necessarily has to comprise the entire or identical amino acid sequence of CD68 or of the extracellular domain of CD68. On the contrary the function of the fusion protein according to the invention is also fulfilled if the first polypeptide comprises a segment or a sequence variant of CD68 or the extracellular domain of CD68, which exerts the LDL binding function of CD68, even in a reduced manner, if applicable. It is known that proteinogenic amino acids can be classified into four groups, namely in polar, non-polar, acidic and basic amino acids. The substitution of a polar amino acid against another polar amino acid, e.g. glycine against serine, as a rule does not cause a change of the biologic activity or does only cause an insignificant change of said biologic activity, that is such an amino acid substitution remains the function of the fusion protein according to the invention largely unaffected. Against this background the present invention also covers such a fusion protein which comprises as the first polypeptide a variant of CD68 or its extracellular domain, where one or several amino acids of one of the mentioned categories of amino acids are substituted by another amino acid of the same category. Such a sequence variant has preferably a homology in relation to the amino acid sequence of CD68 or the extracellular domain of CD68, respectively, of approx. 70%, more preferred of approx. 80%, and highly preferred of approx. 90 to 95%.

It is preferred if the second polypeptide comprises a Fc domain of an immunoglobulin, or a fragment or a variant of the Fc domain, which comprises the dimerization function of the Fc domain.

By this measure it is ensured by an advantageous manner that the fusion protein merely comprises peptide segments which are sufficient for the dimerization of two monomers of the fusion protein according to the invention. “Fc” refers to “fragment crystallizable”. This fragment in addition to the both Fab fragments results from a papain cleavage of the IgG molecule. The Fc domain consists of the paired $C_H2$ and $C_H3$ domains including the hinge region and contains that part of the immunoglobulin which is responsible for the dimerization function. It shall be understood that also a fragment or a variant of the Fc domain can be used without compromising the function of the fusion protein according to the invention, as long as the fragment or the variant, respectively, comprises the dimerization function of an antibody, even in reduced form, if applicable; cf. before mentioned explanations on the fragment or the variant of CD68, which apply to the fragment or the variant of Fc mutatis mutandis.

According to a preferred further development the variant of the Fc domain comprises such a mutation in the complement and Fc receptor binding area which reduces the immunogenicity of the fusion protein according to the invention.

This measure has the advantage that the tolerability of the fusion protein according to the invention is further increased. According to the findings of the inventors it is sufficient for the function of a fusion protein according to the invention if the second polypeptide comprises merely the dimerization function of the Fc domain of the antibody but not the effector function which causes an activation of the immune system. Therefore, for example also a synthetic Fc fragment can be used which is mutated in the complement and Fc receptor binding area in such a manner that an activation of the immune system is largely reduced or even absent.

It is furthermore preferred if the fusion protein comprises an element which connects the first polypeptide to the second polypeptide.

This measure has the advantage that the constructive preconditions are provided which enable the production of the fusion protein according to the invention by means of various expression vectors. The connecting element can be realized by a sequence of amino acids having any composition, however, which preferably comprises one to 100 amino acids. Such a connecting element can also be realized by amino acids which result from the production of the fusion protein according to the invention by ligation of the two polypeptides.

According to a preferred variant the first polypeptide of the fusion protein according to the invention comprises the amino acid sequence SEQ ID No. 1 of the enclosed sequence listing.

By this measure a polypeptide is provided in an advantageous manner which binds to modified LDL or oxLDL, respectively. The amino acid sequence SEQ ID No. 1 is derived from the amino acid sequence of the extracellular domain of the human CD68 protein.

According to a preferred further development the fusion protein comprises a first polypeptide which is encoded by a nucleic acid molecule which comprises the nucleotide sequence SEQ ID No. 2 or 3 of the enclosed listing.

This measure has the advantage that already a coding sequence is provided which encodes the extracellular domain of the human CD68 protein, and which can be easily produced after the introduction into an expression vector via bacteria by means of methods which are known in the art. The nucleotide sequence SEQ ID No. 2 is derived from the nucleotide sequence which encodes the extracellular domain of the human variant of the CD68 protein. The nucleotide sequence SEQ ID No. 3 provides for a polymorphism in the extracellular domain of the human CD68 protein which exists in the population, where a cag base triplet is substituted by an aag base triplet. A functional consequence of this polymorphism is not known.

It shall be understood that not only the nucleotide sequence SEQ ID No. 2 or 3 is suitable for the production of the extracellular domain of the CD68 protein but also variants thereof which, due to the degeneration of the genetic code, encode the same polypeptide. It is known that the genetic code is degenerated since the number of possible codons is larger than the number of amino acids. For most of the amino acids there are more than one codon, e.g. arginine, leucine and serine are encoded by up to six codons. As a general rule the third position in the codon is in parts or fully substitutable. Against this background also such a fusion protein is provided where the first polypeptide is encoded by a nucleic acid molecule which, due to the degeneration of the genetic code, deviates in relation to the nucleotide sequence SEQ ID No. 2 or 3 in individual nucleotide positions, however encodes the extracellular domain of the CD68 protein in an equal manner. Preferably such a variant comprises approx. 70% homology, more preferably approx. 80% homology and highly preferably approx. 90 to 95% homology in relation to the nucleotide sequence SEQ ID No. 2 or 3.

It is preferred if the second polypeptide comprises the amino acid sequence SEQ ID No. 4 of the enclosed sequence listing.

By this measure a second polypeptide which mediates the dimerization is provided in an advantageous manner, which is derived from the Fc fragment of the human IgG1 variant and comprises a mutation in the complement and Fc receptor binding area, which reduces the immunogenicity. By targeted mutagenesis at the position 331 a proline was substituted by a serine and at the amino acid position 234 to 237 the tetrapeptide Leu-Leu-Gly-Gly (SEQ ID NO: 9) was substituted by Ala-Ala-Ala-Ala (SEQ ID NO: 10). To make the expression of the peptide easier in relation with the natural sequence of the Fc fragment of human IgG1 the polypeptide was optimized in its codons with regard to CHO cells.

According to a further development of the invention the second polypeptide is encoded by a nucleic acid molecule which comprises the nucleotide sequence SEQ ID No. 5 of the enclosed sequence listing.

This measure has the advantage that already a nucleotide sequence is provided which encodes the before-described second polypeptide which is derived from the Fc domain of the human IgG1 molecule. After the introduction of the coding sequence into an expression vector appropriate cells, e.g. CHO cells, are transformed by means of methods which are known in the art, which in turn produce the intended second polypeptide. It shall be understood that not only the nucleotide sequence SEQ ID No. 5 is suitable for the production of the second polypeptide but also variants thereof. Such a nucleic acid molecule can also be used which, due to the degeneration of the genetic code, deviates in relation to the nucleotide sequence SEQ ID No. 5 in individual nucleotide positions, however encodes the intended second polypeptide in an equal manner. Preferably such a variant has a homology to the nucleotide sequence SEQ ID No. 5 of approx. 70%, further preferred of approx. 80%, and highly preferred of 90 to 95%.

It is particularly preferred if the fusion protein according to the invention comprises the amino acid sequence SEQ ID No. 6 of the enclosed sequence listing.

By this measure already an entire primary structure of a preferred fusion protein according to the invention is provided, which can easily be produced in a targeted manner either directly by means of peptide synthesis or after the transcription into the coding sequence by molecular biological methods. The amino acid sequence SEQ ID No. 6 does not only comprise the segment of the extracellular domain of CD68 at the N terminus and the segment of the Fc fragment at the C terminus, but also an intermediate element consisting of three amino acids, which connects the extracellular domain of CD68 to the Fc fragment. It shall be understood that within the amino acid sequence SEQ ID No. 6 individual amino acids of one category can be substituted by amino acids of the same category, as this is described further above, without clearly affecting the function of the fusion protein according to the invention. It shall also be understood that the amino acid sequence SEQ ID No. 6 can comprise further amino acids at its N and/or C terminals, which merely serve for a better expression of the fusion protein and to secrete the same from the expressing cells or are merely present for reasons of construction. Such amino acids can e.g. originate from the human IgG kappa chain or from a multiple cloning site (MCS).

It is further preferred if, as the fusion protein according to the invention, such a protein is provided which is encoded by a nucleic acid molecule which comprises the nucleotide sequence SEQ ID No. 7 or 8 of the enclosed sequence listing.

This measure has the advantage that the skilled person is already provided with a coding sequence which encodes a particularly preferred embodiment of the fusion protein according to the invention. The nucleotide sequence SEQ ID No. 7 does also not only comprise coding sequences which encode the extracellular domain of CD68 and the second polypeptide derived from the Fc fragment, but also an intermediate segment which consists of three base triplets and encodes the before-mentioned connecting element. The nucleotide sequence SEQ ID No. 8 provides for the above-mentioned polymorphism in the extracellular CD68 domain so that in relation to the nucleotide sequence SEQ ID No. 7 a cag base triplet is substituted by an aag base triplet. The nucleic acid molecule according to the invention can be introduced into an expression vector by means of methods well known in the art, by which in turn appropriate biological cells, e.g. CHO cells, are transformed, which produce the intended fusion protein. It shall be understood that instead of the nucleotide sequences SEQ ID No. 7 or 8 also variants thereof can be used which, due to the degeneration of the genetic code, encode the same fusion proteins.

According to a preferred further development the fusion protein according to the invention comprises a detectable marker.

This measure has the advantage that the fusion protein can be displayed at the place of its production in vitro but also in vivo by means of imaging methods and it is therefore in particular suited for the identification of e.g. atherosclerotic plaques. A detectable marker according to the invention refers to any component which can be identified by means of imaging methods. This applies to color indicators, such as colorants having fluorescent, phosphorescent or chemiluminescent properties, AMPPD, CSPD, radioactive indicators such $^{32}P$, $^{35}S$, $^{125}I$, $^{131}I$, $^{14}C$, $^{3}H$, non-radioactive indicators such as biotin or digoxigenin, alkaline phosphatase, horseradish peroxidase etc. According to the nature of the marker imaging methods could be autoradiography, blotting, hybridization or microscopic techniques.

Another subject matter of the present invention relates to a homodimer which comprises the before-identified fusion protein according to the invention.

The inventors have realized that the dimerization of the fusion protein according to the invention results in an activity which is many times higher. This has the advantage that e.g. CHO cell lines which are transformed by an expression vector that encodes the fusion protein according to the invention, secrete a soluble dimer which comprises two fusion proteins which are crosslinked by bisulfide bridges in the region of the second polypeptide, e.g. in the region of the Fc domain. Thereby it has turned out that with such a homodimer in relation to a monomer the affinity for modified LDL, in particular for oxLDL, is remarkably increased. The inventors have evidences that the homodimers after a systemic application into a living being rapidly and specifically accumulate exclusively at pre-damaged or atherosclerotically altered vascular areas and that a rapid degradation in the blood as well as any unspecific systemic side effects can be largely avoided. The inventors have further evidences that the homodimer according to the invention causes also a deactivation or blockage of the native CD68 receptors in the living being, by which the LDL endocytosis by macrophages and the transformation into foam cells can be additionally prevented. Such a mechanism is already described in the art for other soluble scavenger receptors, such as SR-A1; cf. Gough et al. (2001), The use of human CD68 transcriptional regulatory sequences to direct high-level expression of class A scavenger receptor in macrophages in vitro and in vivo, Immunology 103, pages 351 to 361. The inventors were able to demonstrate in co-cultivation assays in vitro that the addition of increasing concentrations of the homodimer according to the invention results in a significant inhibition of the formation of foam cells and that several functions of foam cells, such as the secretion of MMP-9, can be inhibited.

Against this background another subject matter according to the invention relates to a nucleic acid molecule which encodes the before-identified fusion protein according to the invention. The nucleic acid molecule according to the invention comprises preferably (a) a first nucleotide sequence which encodes a polypeptide which specifically binds to modified LDL, preferably to oxLDL, and (b) a second nucleotide sequence which encodes a polypeptide which mediates a dimerization. The nucleic acid molecule according to the invention comprises preferably the nucleotide sequence SEQ ID No. 2 or 3, No. 5, or No. 7, or 8, respectively, of the enclosed sequence listing, or in each case a variant thereof, which encodes, due to the degeneration of the genetic code, the same polypeptide. It shall be understood that the nucleic acid molecule can comprise further nucleotide segments which enable or favor e.g. an expression or production in correspondingly transformed cells. For example a leader segment of the kappa chain of the IgG molecule and amino acids connected thereto resulting from the multiple cloning site (MCS) for constructive reasons can be arranged at the 5' end, which however in the translation product might be cleaved off from the entire construct and might therefore not necessarily be present in the fusion protein according to the invention.

Another subject matter of the present invention relates to a pharmaceutical and/or diagnostic composition which comprises the fusion protein according to the invention and/or the homodimer according to the invention and/or the nucleic acid molecule according to the invention as well as a pharmaceutically and/or diagnostically acceptable carrier, if applicable, and further pharmaceutically and/or diagnostically effective additives, if applicable.

Diagnostically and pharmaceutically acceptable carriers and any further additives are generally known in the art and are e.g. described in the essay of Kibbe A., Handbook of Pharmaceutical Excipients, Third Edition, American Pharmaceutical Association and Pharmaceutical Press 2000. According to the invention additives comprise any compound or composition which are advantageous for a diagnostic or therapeutic use of the composition, including salts, binding agents and further substances involved in the formulation of medicaments.

Another subject matter of the present invention relates to the use of the fusion protein according to the invention and/or the homodimer according to the invention and/or the protein acid molecule according to the invention for the production of a pharmaceutical and/or diagnostic composition for the treatment and/or diagnosis of acute or chronic vascular diseases, including atherosclerosis, atherosclerotic plaques, cardiac infarction, apoplexy and peripheral artery occlusive disease (PAOD).

The invention is further realized in a method for the production of a pharmaceutical and/or diagnostic composition for the treatment and/or diagnosis of before-mentioned diseases, which comprises the following steps: (a) Provision of the fusion protein according to the invention and/or of the homodimer according to the invention and/or the nucleic acid molecule according to the invention; (b) formulation into a pharmaceutically and/or diagnostically acceptable carrier, and, if applicable, (c) addition of further pharmaceutically and/or diagnostically active additives.

Another subject matter of the present invention relates to a method for the diagnosis of acute or chronic vascular diseases, including atherosclerosis, atherosclerotic plaques, cardiac infarction, apoplexy and PAOD in a living being, comprising the following steps: (1) Provision of a fusion protein according to the invention and/or a homodimer according to the invention, which comprises a detectable marker, (2) introduction of the fusion protein and/or of the homodimer into the living being, and (3) visualization of the specific accumulation of the fusion protein in the living being by means of imaging methods, such as the positron emission tomography (PET).

By means of this method atherosclerotic plaques or high concentrations of modified LDL, including oxLDL, can be detected due to the selective accumulation of the fusion protein according to the invention or the homodimer according to the invention, which enables a reliable diagnosis of corresponding vascular diseases or a predisposition therefor. So far the activity and stability of atherosclerotic plaques are not well detectable by means of angiography, application of contrast medium and the determination of the size of the lumen of the vessel, which are usually used in the art. The present invention provides effective remedy.

Another subject matter of the present invention relates to a method for the production of the fusion protein according to the invention, which comprises the following steps: (1) Provision of a first nucleotide sequence encoding a polypeptide which specifically binds to modified LDL, preferably to oxLDL, (2) provision of a second nucleotide sequence encoding for a polypeptide which mediates the dimerization, (3) ligation of the first and the second nucleotide sequence to obtain a fusion sequence encoding the fusion protein, (4) cloning of the fusion sequence into an expression vector, (5) introduction of the expression vector in a cell suitable for the expression, (6) expression of the fusion protein in the cell, and (7) isolation of the fusion protein from the cell.

By means of this method also the homodimer according to the invention can be produced, since suitable cells, e.g. HEK or CHO cells which are transformed according to step (5), already produce after the expression according to step (6) a homodimer which comprises disulfide bridges in the second polypeptide, which connect the two fusion proteins according to the invention, to each other. The homodimer is secreted by the cells into the extracellular medium.

It shall be understood that the before-mentioned features and those to be explained in the following cannot only be used in the combination indicated in each case but also in other combinations or separately, without departing from the scope of the present invention.

The present invention is now explained in detail by means of embodiments which are of pure exemplary nature and do not limit the scope of the invention. Reference is made to the enclosed figures:

DESCRIPTION OF PREFERRED EMBODIMENTS

1. Nucleotide and Amino Acid Sequences

Figure 1:
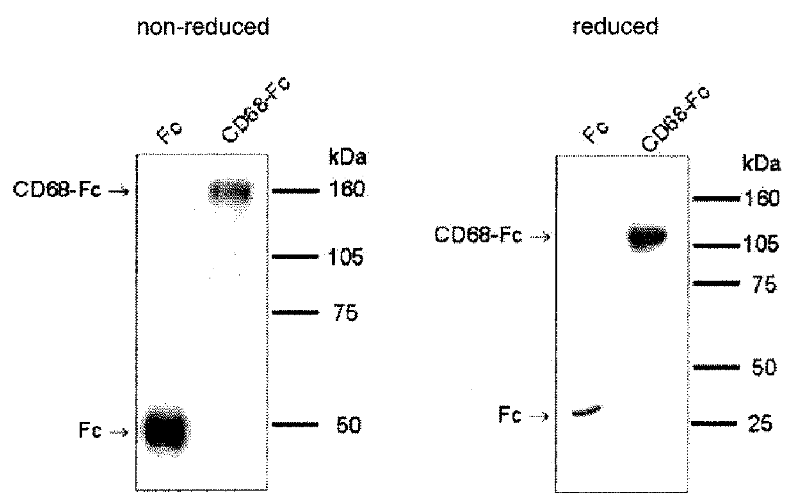
FIG. 1: Detection of the fused dimeric CD68-Fc fusion protein by Western Blot analysis.

The common one-letter codes are used in each case. In the presentation the amino acid sequences comprise at their left end the amino or N terminal end, and at their right end the carboxy or C terminal end. The nucleotide sequences comprise at their left end the 5' end, and at their right end the 3' end.

1.1 Amino Acid Sequence of the Extracellular Domain of CD68 Comprising the Polymorphism 1 (Glutamine) (SEQ ID No. 1)

```
NDCPHKKSATLLPSFTVTPTVTESTGTTSHRTTKSHKTTTHRTTTTGTTS

HGPTTATHNPTTTSHGNVTVHPTSNSTATSQGPSTATHSPATTSHGNATV

HPTSNSTATSPGFTSSAHPEPPPPSPSPSPTSKETIGDYTWTNGSQPCVH

LQAQIQIRVMYTTQGGGEAWGISVLNPNKTKVQGSCEGAHPHLLLSFPYG

HLSFGFMQDLQQKVVYLSYMAVEYNVSFPHAAQWTFSAQNASLRDLQAPL
```

-continued

GQSFSCSNSSIILSPAVHLDLLSLRLQAAQLPHTGVFGQSFSCPSDRS 1.2 Nucleotide Sequence Encoding the Extracellular Domain of CD68, Polymorphism 1 (SEQ ID No. 2)

AATGACTGTCCTCACAAAAAATCAGCTACTTTGCTGCCATCCTTCACGGT
GACACCCACGGTTACAGAGAGCACTGGAACAACCAGCCACAGGACTACCA
AGAGCCACAAAACCACCACTCACAGGACAACCACCACAGGCACCACCAGC
CACGGACCCACGACTGCCACTCACAACCCCACCACCACCAGCCATGGAAA
CGTCACAGTTCATCCAACAAGCAATAGCACTGCCACCAGCCAGGGACCCT
CAACTGCCACTCACAGTCCTGCCACCACTAGTCATGGAAATGCCACGGTT
CATCCAACAAGCAACAGCACTGCCACCAGCCCAGGATTCACCAGTTCTGC
CCACCCAGAACCACCTCCACCCTCTCCGAGTCCTAGCCCAACCTCCAAGG
AGACCATTGGAGACTACACGTGGACCAATGGTTCCCAGCCCTGTGTCCAC
CTCCAAGCCCAGATTCAGATTCGAGTCATGTACACAACCCAGGGTGGAGG
AGAGGCCTGGGGCATCTCTGTACTGAACCCCAACAAAACCAAGGTCCAGG
GAAGCTGTGAGGGTGCCCATCCCCACCTGCTTCTCTCATTCCCCTATGGA
CACCTCAGCTTTGGATTCATGCAGGACCTCCAGCAGAAGGTTGTCTACCT
GAGCTACATGGCGGTGGAGTACAATGTGTCCTTCCCCCACGCAGCACAGT
GGACATTCTCGGCTCAGAATGCATCCCTTCGAGATCTCCAAGCACCCCTG
GGGCAGAGCTTCAGTTGCAGCAACTCGAGCATCATTCTTTCACCAGCTGT
CCACCTCGACCTGCTCTCCCTGAGGCTCCAGGCTGCTCAGCTGCCCCACA
CAGGGGTCTTTGGGCAAAGTTTCTCCTGCCCCAGTGACCGGTCC

The polymorphism 1 is indicated in bold letters.

1.3 Nucleotide Sequence Encoding the Extracellular Domain of CD68, Polymorphism 2 (SEQ ID No. 3)

AATGACTGTCCTCACAAAAAATCAGCTACTTTGCTGCCATCCTTCACGGT
GACACCCACGGTTACAGAGAGCACTGGAACAACCAGCCACAGGACTACCA
AGAGCCACAAAACCACCACTCACAGGACAACCACCACAGGCACCACCAGC
CACGGACCCACGACTGCCACTCACAACCCCACCACCACCAGCCATGGAAA
CGTCACAGTTCATCCAACAAGCAATAGCACTGCCACCAGCCAGGGACCCT
CAACTGCCACTCACAGTCCTGCCACCACTAGTCATGGAAATGCCACGGTT
CATCCAACAAGCAACAGCACTGCCACCAGCCCAGGATTCACCAGTTCTGC
CCACCCAGAACCACCTCCACCCTCTCCGAGTCCTAGCCCAACCTCCAAGG
AGACCATTGGAGACTACACGTGGACCAATGGTTCCCAGCCCTGTGTCCAC
CTCCAAGCCCAGATTCAGATTCGAGTCATGTACACAACCCAGGGTGGAGG
AGAGGCCTGGGGCATCTCTGTACTGAACCCCAACAAAACCAAGGTCCAGG
GAAGCTGTGAGGGTGCCCATCCCCACCTGCTTCTCTCATTCCCCTATGGA
CACCTCAGCTTTGGATTCATGCAGGACCTCCAGCAGAAGGTTGTCTACCT
GAGCTACATGGCGGTGGAGTACAATGTGTCCTTCCCCCACGCAGCAAAGT
GGACATTCTCGGCTCAGAATGCATCCCTTCGAGATCTCCAAGCACCCCTG
GGGCAGAGCTTCAGTTGCAGCAACTCGAGCATCATTCTTTCACCAGCTGT

-continued

CCACCTCGACCTGCTCTCCCTGAGGCTCCAGGCTGCTCAGCTGCCCCACA
CAGGGGTCTTTGGGCAAAGTTTCTCCTGCCCCAGTGACCGGTCC

The polymorphism 2 is indicated in bold letters.

1.4 Amino Acid Sequence of the Second Polypeptide Derived from the Fc Domain, which Mediates the Dimerization (SEQ ID No. 4)

ESKSCDKTHTCPPCPAPEAAAAPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPASIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK 1.5 Nucleotide Sequence Encoding the Second Polypeptide Derived from the Fc Domain, and which Mediates the Dimerization (SEQ ID No. 5)

GAGTCTAAGTCCTGTGATAAGACTCATACCTGCCCCCCCTGCCCAGCACC
CGAGGCAGCAGCCGCCCCCTCAGTGTTTCTCTTCCCTCCAAAACCCAAGG
ATACCCTGATGATCAGCCGTACACCTGAGGTCACCTGCGTAGTCGTCGAT
GTGTCTCACGAGGACCCGGAGGTGAAGTTTAATTGGTATGTGGACGGGGT
AGAAGTGCATAATGCCAAGACTAAACCTCGAGAGGAACAATATAACTCCA
CCTATAGGGTGGTCAGCGTTCTCACGGTCCTTCACCAGGACTGGTTGAAT
GGAAAGGAATACAAGTGTAAGGTGAGCAACAAAGCCCTGCCCGCTTCCAT
AGAAAAGACAATCTCCAAAGCTAAAGGGCAGCCACGGGAACCTCAGGTGT
ACACCCTGCCGCCTAGCAGAGATGAGCTCACAAAGAACCAGGTGTCTCTG
ACATGCTTGGTGAAGGGTTTCTATCCTTCGGACATTGCCGTTGAGTGGGA
AAGTAACGGCCAGCCTGAGAATAACTACAAGACCACACCACCCGTTCTTG
ACTCTGATGGGAGTTTCTTTTTGTACAGTAAGTTAACTGTCGACAAATCA
CGCTGGCAGCAAGGAAATGTTTTCTCTTGTTCCGTGATGCACGAGGCACT
GCACAACCATTACACTCAGAAATCCCTGAGCCTATCACCAGGCAAATAA 1.6 Amino Acid Sequence of the Entire CD68-Fc Construct, Including the Connecting Element (SEQ ID No. 6)

NDCPHKKSATLLPSFTVTPTVTESTGTTSHRTTKSHKTTTHRTTTTGTTS
HGPTTATHNPTTTSHGNVTVHPTSNSTATSQGPSTATHSPATTSHGNATV
HPTSNSTATSPGFTSSAHPEPPPPSPSPSPTSKETIGDYTWTNGSQPCVH
LQAQIQIRVMYTTQGGGEAWGISVLNPNKTKVQGSCEGAHPHLLLSFPYG
HLSFGFMQDLQQKVVYLSYMAVEYNVSFPHAAQWTFSAQNASLRDLQAPL
GQSFSCSNSSIILSPAVHLDLLSLRLQAAQLPHTGVFGQSFSCPSDRSGG
RESKSCDKTHTCPPCPAPEAAAAPSVFLFPPKPKDTLMISRTPEVTCVVV
DVSHEDPEVKFNWYVDGVEVHNAKTKPREEQYNSTYRVVSVLTVLHQDWL
NGKEYKCKVSNKALPASIEKTISKAKGQPREPQVYTLPPSRDELTKNQVS
LTCLVKGFYPSDIAVEWESNGQPENNYKTTPPVLDSDGSFFLYSKLTVDK
SRWQQGNVFSCSVMHEALHNHYTQKSLSLSPGK

The connecting element is underlined. Ahead of the connecting element (towards the N terminus) the segment of the extracellular domain of CD68 is located, following the connecting element (towards the C terminals) the segment of the polypeptide is located which is derived from the Fc domain and which mediates the dimerization.

1.7 Nucleotide Sequence Encoding the Entire Construct Inclusive the Connecting Element, Polymorphism 1 (SEQ ID No. 7)

AATGACTGTCCTCACAAAAAATCAGCTACTTTGCTGCCATCCTTCACGGT

GACACCCACGGTTACAGAGAGCACTGGAACAACCAGCCACAGGACTACCA

AGAGCCACAAAACCACCACTCACAGGACAACCACCACAGGCACCACCAGC

CACGGACCCACGACTGCCACTCACAACCCCACCACCACCAGCCATGGAAA

CGTCACAGTTCATCCAACAAGCAATAGCACTGCCACCAGCCAGGGACCCT

CAACTGCCACTCACAGTCCTGCCACCACTAGTCATGGAAATGCCACGGTT

CATCCAACAAGCAACAGCACTGCCACCAGCCCAGGATTCACCAGTTCTGC

CCACCCAGAACCACCTCCACCCTCTCCGAGTCCTAGCCCAACCTCCAAGG

AGACCATTGGAGACTACACGTGGACCAATGGTTCCCAGCCCTGTGTCCAC

CTCCAAGCCCAGATTCAGATTCGAGTCATGTACACAACCCAGGGTGGAGG

AGAGGCCTGGGGCATCTCTGTACTGAACCCCAACAAAACCAAGGTCCAGG

GAAGCTGTGAGGGTGCCCATCCCCACCTGCTTCTCTCATTCCCCTATGGA

CACCTCAGCTTTGGATTCATGCAGGACCTCCAGCAGAAGGTTGTCTACCT

GAGCTACATGGCGGTGGAGTACAATGTGTCCTTCCCCCACGCAGCACAGT

GGACATTCTCGGCTCAGAATGCATCCCTTCGAGATCTCCAAGCACCCCTG

GGGCAGAGCTTCAGTTGCAGCAACTCGAGCATCATTCTTTCACCAGCTGT

CCACCTCGACCTGCTCTCCCTGAGGCTCCAGGCTGCTCAGCTGCCCCACA

CAGGGGTCTTTGGGCAAAGTTTCTCCTGCCCCAGTGACCGGTCCGGCGGC

CGCGAGTCTAAGTCCTGTGATAAGACTCATACCTGCCCCCCCTGCCCAGC

ACCCGAGGCAGCAGCCGCCCCCTCAGTGTTTCTCTTCCCTCCAAAACCCA

AGGATACCCTGATGATCAGCCGTACACCTGAGGTCACCTGCGTAGTCGTC

GATGTGTCTCACGAGGACCCGGAGGTGAAGTTTAATTGGTATGTGGACGG

GGTAGAAGTGCATAATGCCAAGACTAAACCTCGAGAGGAACAATATAACT

CCACCTATAGGGTGGTCAGCGTTCTCACGGTCCTTCACCAGGACTGGTTG

AATGGAAAGGAATACAAGTGTAAGGTGAGCAACAAAGCCCTGCCCGCTTC

CATAGAAAAGACAATCTCCAAAGCTAAAGGGCAGCCACGGGAACCTCAGG

TGTACACCCTGCCGCCTAGCAGAGATGAGCTCACAAAGAACCAGGTGTCT

CTGACATGCTTGGTGAAGGGTTTCTATCCTTCGGACATTGCCGTTGAGTG

GGAAAGTAACGGCCAGCCTGAGAATAACTACAAGACCACACCACCCGTTC

TTGACTCTGATGGGAGTTTCTTTTTGTACAGTAAGTTAACTGTCGACAAA

TCACGCTGGCAGCAAGGAAATGTTTTCTCTTGTTCCGTGATGCACGAGGC

ACTGCACAACCATTACACTCAGAAATCCCTGAGCCTATCACCAGGCAAAT

AA

The coding sequence for the connecting element is underlined. Following the coding sequence of the connecting element (towards the N terminus) the segment is located which encodes the extracellular domain of CD68, whereby the polymorphism is indicated in bold letters, following the coding sequence of the connecting element (towards the C terminus) the segment is located which encodes the second polypeptide which is derived from the Fc fragment and mediates the dimerization.

1.8 Nucleotide Sequence Encoding the Entire Construct Including the Connecting Element, Polymorphism 2 (SEQ ID No. 8)

AATGACTGTCCTCACAAAAAATCAGCTACTTTGCTGCCATCCTTCACGGT

GACACCCACGGTTACAGAGAGCACTGGAACAACCAGCCACAGGACTACCA

AGAGCCACAAAACCACCACTCACAGGACAACCACCACAGGCACCACCAGC

CACGGACCCACGACTGCCACTCACAACCCCACCACCACCAGCCATGGAAA

CGTCACAGTTCATCCAACAAGCAATAGCACTGCCACCAGCCAGGGACCCT

CAACTGCCACTCACAGTCCTGCCACCACTAGTCATGGAAATGCCACGGTT

CATCCAACAAGCAACAGCACTGCCACCAGCCCAGGATTCACCAGTTCTGC

CCACCCAGAACCACCTCCACCCTCTCCGAGTCCTAGCCCAACCTCCAAGG

AGACCATTGGAGACTACACGTGGACCAATGGTTCCCAGCCCTGTGTCCAC

CTCCAAGCCCAGATTCAGATTCGAGTCATGTACACAACCCAGGGTGGAGG

AGAGGCCTGGGGCATCTCTGTACTGAACCCCAACAAAACCAAGGTCCAGG

GAAGCTGTGAGGGTGCCCATCCCCACCTGCTTCTCTCATTCCCCTATGGA

CACCTCAGCTTTGGATTCATGCAGGACCTCCAGCAGAAGGTTGTCTACCT

GAGCTACATGGCGGTGGAGTACAATGTGTCCTTCCCCCACGCAGCAAAGT

GGACATTCTCGGCTCAGAATGCATCCCTTCGAGATCTCCAAGCACCCCTG

GGGCAGAGCTTCAGTTGCAGCAACTCGAGCATCATTCTTTCACCAGCTGT

CCACCTCGACCTGCTCTCCCTGAGGCTCCAGGCTGCTCAGCTGCCCCACA

CAGGGGTCTTTGGGCAAAGTTTCTCCTGCCCCAGTGACCGGTCCGGCGGC

CGCGAGTCTAAGTCCTGTGATAAGACTCATACCTGCCCCCCCTGCCCAGC

ACCCGAGGCAGCAGCCGCCCCCTCAGTGTTTCTCTTCCCTCCAAAACCCA

AGGATACCCTGATGATCAGCCGTACACCTGAGGTCACCTGCGTAGTCGTC

GATGTGTCTCACGAGGACCCGGAGGTGAAGTTTAATTGGTATGTGGACGG

GGTAGAAGTGCATAATGCCAAGACTAAACCTCGAGAGGAACAATATAACT

CCACCTATAGGGTGGTCAGCGTTCTCACGGTCCTTCACCAGGACTGGTTG

AATGGAAAGGAATACAAGTGTAAGGTGAGCAACAAAGCCCTGCCCGCTTC

CATAGAAAAGACAATCTCCAAAGCTAAAGGGCAGCCACGGGAACCTCAGG

TGTACACCCTGCCGCCTAGCAGAGATGAGCTCACAAAGAACCAGGTGTCT

CTGACATGCTTGGTGAAGGGTTTCTATCCTTCGGACATTGCCGTTGAGTG

GGAAAGTAACGGCCAGCCTGAGAATAACTACAAGACCACACCACCCGTTC

TTGACTCTGATGGGAGTTTCTTTTTGTACAGTAAGTTAACTGTCGACAAA

TCACGCTGGCAGCAAGGAAATGTTTTCTCTTGTTCCGTGATGCACGAGGC

ACTGCACAACCATTACACTCAGAAATCCCTGAGCCTATCACCAGGCAAAT

AA

The coding sequence for the connecting element is underlined. Following the coding sequence for the connecting element (towards the N terminus) the segment is located which encodes the extracellular domain of CD68, whereby the polymorphism 2 is indicated in bold letters, following the coding sequence for the connecting element (towards the C terminus) the segment is located which encodes the second polypeptide which is derived from the Fc fragment and mediates the dimerization.

2. Cloning of the CD68-Fc Fusion Protein

The extracellular domain of human CD68 was amplified from a freshly prepared macrophages cDNA library by means of a polymerase chain reaction (PCR) by using specific primers. At the ends of the fragment new restriction sites were introduced. The fragment was cloned into a plasmid which comprises a leader sequence of the kappa chain of human Ig, by which the leader sequence of CD68 was replaced, to improve the secretion. An artificial gene was synthesized which is derived from the Fc domain of human IgG1. By targeted mutagenesis at the position 331 a proline was substituted by a serine and at the amino acid positions 234 to 237 the tetrapeptide Leu-Leu-Gly-Gly (SEQ ID NO: 9) was substituted by Ala-Ala-Ala-Ala (SEQ ID NO: 10). To facilitate the expression of the peptide this polypeptide was optimized for CHO cells with regards to its codons. The two fragments were in each case digested with restriction enzymes and ligated, that the Fc portion is joined to the CD68 portion. This resulted in a specific connecting sequence between the two parts of the fusion proteins, which consist of three amino acids. In the following the fusion cDNA resulting therefrom is shown (SEQ ID NO: 11):

ATGGAGACAGACACACTCCTGCTATGGGTACTGCTGCTCTGGGTTCCAGGTTCCACTGGT

GACGCGGCCCAGCCGGCCAGGCGCGCGCCGTACGAAGCTTaatgactgtcctcacaaaaaatcagctactttgctgccatccttcacggtgacacccacggttacagagagcactggaacaaccagccacaggactaccaagagccacaaaaccaccactcacaggacaaccaccacaggcaccaccagccacggacccacgactgccactcacaaccccaccaccaccagccatggaaacgtcacagttcatccaacaagcaatagcactgccaccagccagggaccctcaactgccactcacagtcctgccaccactagtcatggaaatgccacggttcatccaacaagcaacagcactgccaccagcccaggattcaccagttctgcccacccagaaccacctccaccctctccgagtcctagcccaacctccaaggagaccattggagactacacgtggaccaatggttcccagccctgtgtccacctccaagcccagattcagattcgagtcatgtacacaacccagggtggaggagaggcctggggcatctctgtactgaaccccaacaaaaccaaggtccagggaagctgtgagggtgcccatccccacctgcttctctcattcccctatggacacctcagctttggattcatgcaggacctccagcagaaggttgtctacctgagctacatggcggtggagtacaatgtgtccttcccccacgcagcacagtggacattctcggct cag/aag polymorphism cagaatgcatcccttcgagatctccaagcaccccctggggcagagcttcagttgcagcaac tcgagcatcattctttcaccagctgtccacctcgacctgctctccctgaggctccaggct gctcagctgccccacacaggggtctttgggcaaagtttctcctgccccagtgaccggtcc

GGCGGCCGCGAGTCTAAGTCCTGTGATAAGACTCATACCTGCCCCCCCTGCCCAGCACCC

GAGGCAGCAGCCGCCCCCTCAGTGTTTCTCTTCCCTCCAAAACCCAAGGATACCCTGATG

ATCAGCCGTACACCTGAGGTCACCTGCGTAGTCGTCGATGTGTCTCACGAGGACCCGGAG

GTGAAGTTTAATTGGTATGTGGACGGGGTAGAAGTGCATAATGCCAAGACTAAACCTCGA

GAGGAACAATATAACTCCACCTATAGGGTGGTCAGCGTTCTCACGGTCCTTCACCAGGAC

TGGTTGAATGGAAAGGAATACAAGTGTAAGGTGAGCAACAAAGCCCTGCCCGCTTCCATA

GAAAAGACAATCTCCAAAGCTAAAGGGCAGCCACGGGAACCTCAGGTGTACACCCTGCCG

CCTAGCAGAGATGAGCTCACAAAGAACCAGGTGTCTCTGACATGCTTGGTGAAGGGTTTC

TATCCTTCGGACATTGCCGTTGAGTGGGAAAGTAACGGCCAGCCTGAGAATAACTACAAG

ACCACACCACCCGTTCTTGACTCTGATGGGAGTTTCTTTTTGTACAGTAAGTTAACTGTC

GACAAATCACGCTGGCAGCAAGGAAATGTTTTCTCTTGTTCCGTGATGCACGAGGCACTG

CACAACCATTACACTCAGAAATCCCTGAGCCTATCACCAGGCAAATAA

The IgG leader (human Ig kappa chain) including amino acids from the MCS for constructive reasons are shown in the first part of the molecule in capital and bold letters (IgG leader) and underlined (MCS), in the following the extracellular domain of human CD68 is shown in lower case letters, a cag-aag polymorphism is indicated in bold letters; in the following a connecting segment is shown, which comprises nine nucleotides and is printed in bold letters and underlined; in the following the coding sequence or the polypeptide derived from the Fc fragment are shown, which was optimized for CHO in view of their codons and which is mutated in complement and Fc receptor area.

The encoded fusion protein is schematically shown in the following (SEQ ID NO: 12):

```
      Leader peptide         MCS spacer         CD68
  1   METDTLLLWV LLLWVPGSTG DAAQPARRAR RTKLNDCPHK KSATLLPSFT

 51   VTPTVTESTG TTSHRTTKSH KTTTHRTTTT GTTSHGPTTA THNPTTTSHG

101   NVTVHPTSNS TATSQGPSTA THSPATTSHG NATVHPTSNS TATSPGFTSS

151   AHPEPPPPSP SPSPTSKETI GDYTWTNGSQ PCVHLQAQIQ IRVMYTTQGG

201   GEAWGISVLN PNKTKVQGSC EGAHPHLLLS FPYGHLSFGF MQDLQQKVVY

251   LSYMAVEYNV SFPHAAQWTF SAQNASLRDL QAPLGQSFSC SNSSIILSPA

301   VHLDLLSLRL QAAQLPHTGV FGQSFSCPSD RSGGRESKSC DKTHTCPPCP

                                      connection      hIgGlmut
351   APEAAAAPSV FLFPPKPKDT LMISRTPEVT CVVVDVSHED PEVKFNWYVD

401   GVEVHNAKTK PREEQYNSTY RVVSVLTVLH QDWLNGKEYK CKVSNKALPA

451   SIEKTISKAK GQPREPQVYT LPPSRDELTK NQVSLTCLVK GFYPSDIAVE

501   WESNGQPENN YKTTPPVLDS DGSFFLYSKL TVDKSRWQQG NVFSCSVMHE

551   ALHNHYTQKS LSLSPGK*
```

The leader peptide is shown in bold letters (this segment is preferably not present in the fusion protein according to the invention or only parts thereof), followed by the MCS spacer which is underlined (this segment can also be absent, however, might also be present in the fusion protein according to the invention), followed by the extracellular domain of human CD68, followed by the connecting element comprising three amino acids, which is also underlined, followed by the polypeptide derived from the Fc fragment of the human IgG1 molecule, which is optimized for CHO in view of its codons and is mutated in the complement and Fc receptor binding area (hIgG1mut). "*" at the carboxy terminal end represents the stop codon.

The fusion cDNA was again digested by restriction enzymes and introduced into a pcDNA5 plasmid vector (Invitrogen) by means of conventional cloning. The resulting plasmid vector is designated as pcDNA5-FRT-CD68-Fc-opt.

3. Production of CHO Cells which Express the CD68-Fc Fusion Protein in a Stable Manner Flp-In™-CHO cells (invitrogen) at a confluence of 70% were co-transfected with the plasmids pOG44:pcDNA5-FRT-CD68-Fc-opt (both Invitrogen) in the ratio of 9:1. 24 hours after the transfection the cells were washed and fresh media was added. 48 hours after the transfection the cells were transferred 1:20 into fresh medium containing 500 mg/ml hygromycin. Hygromycin resistant foci were isolated and expanded.

The expanded transformants were analyzed for the expression of the CD68-Fc fusion protein (FIG. 1: CD68-Fc) by means of Western Blot analysis (SDS-PAGE) by the use of antibodies directed against human Fc. A secondary anti-human Fc antibody was used. Fc protein was used as a control (FIG. 1: Fc), which did not comprise an extracellular CD68 domain. For CD68-Fc under non-reducing conditions a specific band at 160 kDa (FIG. 1, left) and under reducing conditions at 115 kDa (FIG. 1, right) was shown.

Furthermore a quantitative detection was performed by means of a human IgG-ELISA. Herewith in the cell culture supernatants of the producing CHO cell line a concentration of CD68-Fc of about 2 mg/ml could be detected, whereas with the wild type cells no CD68-Fc fusion protein could be detected.

4. Purification of the CD68 Fusion Protein

The CHO cells which express the CD68-Fc fusion protein in a stable manner were cultivated. Three days after the infection the culture supernatant was centrifuged at 3800 g for 30 minutes at 4° C. and filtrated through a filter having a pore size of 0.2 μm. The CD68 fusion protein was precipitated by the addition of 1.2 volumina of ammonium sulfate (761 g/l) and shaking over night at 4° C.

The proteins were pelleted by centrifugation at 3000 g for 30 minutes at 4° C., dissolved in 0.1 volumina PBS and dialyzed in PBS at 4° C. over night. The protein solution was cleared by centrifugation at 14000 g for 30 minutes at 4° C. and filtration through a filter having a pore size of 0.2 μm and loaded onto a protein A column (HiTrap™) protein A HP, (Amersham Pharmacia Wiotech AB, Upsalla, Sweden) which was previously equilibrated with binding buffer (20 mM sodium phosphate buffer pH 7.0, 0.02% $NaN_3$). The column was washed with binding buffer up to a $OD_{280}$<0.01 and eluted with elution buffer (100 mM glycine pH 2.7).

The eluted fractions of 900 μl each were neutralized with 100 μl neutralization buffer (1 M Tris-HCl pH 9.0, 0.02% $NaN_3$), pooled, dialyzed in PBS at 4° C. over night, aliquoted and freezed at −20° C. The column was neutralized with binding buffer, washed with 20% (v/v) of ethanol and stored in a refrigerator.

5. Differentiation of $CD34^+$ Stem Cells into Foam Cells by Co-Cultivation with Thrombocytes To isolate human thrombocytes venous blood was withdrawn from healthy test persons and collected into acidic citrate dextrose (ACD) buffer. After the centrifugation at 430 g for 20 minutes the platelet-rich plasma (PRP) was removed, added to Tyrodes HEPES buffer (2.5 mM HEPES, 150 mM NaCl, 1 mM HCl, 2.5 mM $NaHCO_3$, 0.36 mM $NaH_2PO_4$, 5.5 mM glucose, 1 mg/ml BSA, pH 6.5) and centrifuged at 900 g for 10 minutes. After the removal of the supernatant the thrombocyte containing pellet was suspended in Tyrodes HEPES buffer (pH 7.4).

This method results in a high purity of the thrombocytes without a measurable contamination by polymorph nuclear cells or monocytes, which was verified by the absence of CD14 (flow cytometry and myeloperoxydase-ELISA). The before-mentioned method is described in Langer H. et al. (2006; electronically 2005), Adherent platelets recruit and induce differentiation of murine embryonic endothelial progenitor cells to mature endothelial cells in vitro, Circ. Res. 98(2): e2-10.

Human $CD34^+$ cells were isolated from human cord blood. This was obtained after the approval of the local ethics committee from healthy women immediately after the birth of a child. At least 95% of the isolated cells were positive for $CD34^+$ which was confirmed by means of flow cytometry analysis after each isolation. Human mononuclear cells were also obtained from cord blood by density gradient centrifugation on the Biocoll separation solution (BIOCROM Berlin, Germany) at 600 g for 15 minutes. $CD34^+$ cells were enriched by immunoaffinity selection (CD34 progenitor cell isolation kit; Milteenyi Biotec, Bergisch Gladbach, Germany) according to the manual of the producer. In the following the cells were incubated on 96 well plates which were covered with 0.2% gelatine. For the cultivation of the cells IMDM with glutamax, supplemented with 5% heat-inactivated fetal calf serum, 100 mg/ml penicillin-streptomycin, 1% MEM vitamins and 1% non-essential amino acids were used, all purchased from Gibco (Invitrogen, Karlsruhe, Germany). $CD34^+$ progenitor cells (50000 cells) were co-cultivated at 37° C. and 5% $CO_2$ with thrombocytes ($2\times10^8$-ml) in 96 well plates which were pre-covered with 0.2% gelatine. The formation of foam cells was counted in six windows by means of phase contrast microscopy.

Figure 2A:
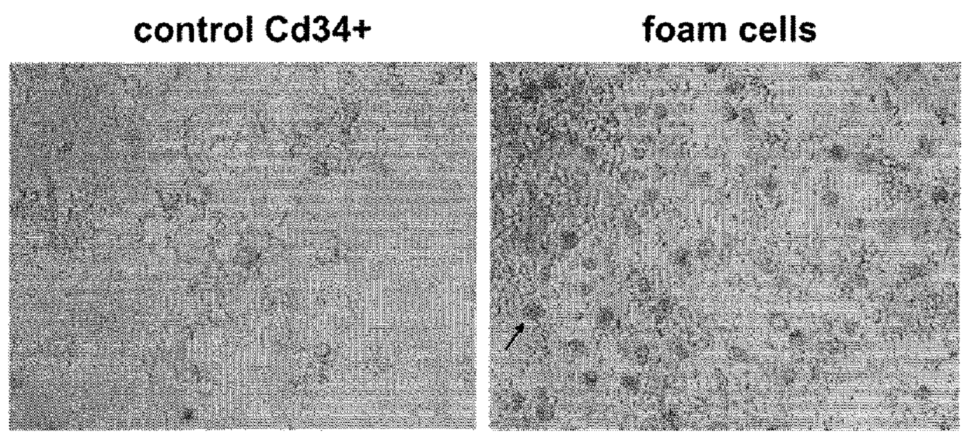
FIG. 2: Differentiation of $CD34^+$ stem cells into foam cells after 10 days of co-cultivation with thrombocytes.
Figure 2B:
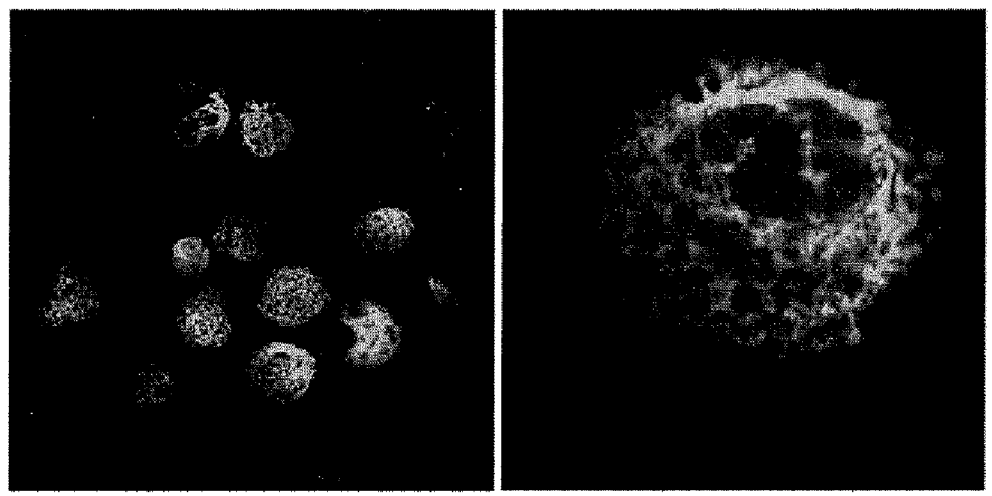
Figure 2C:
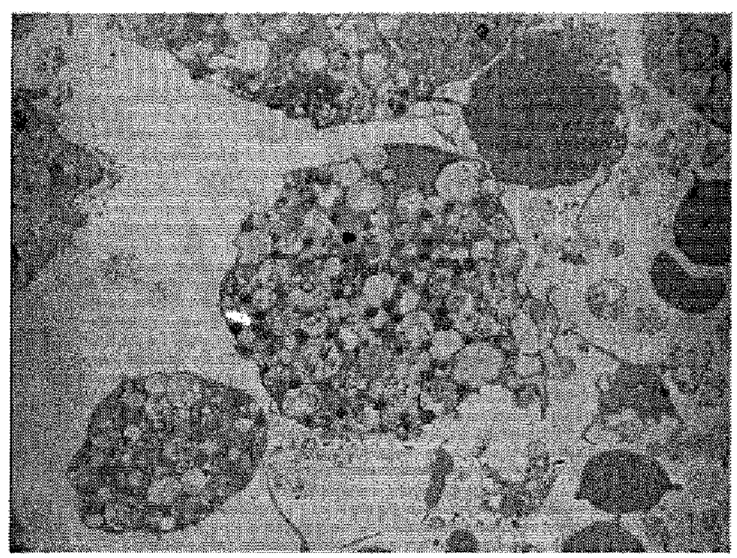

The phase contrast microscopy showed a differentiation of $CD34^+$ stem cells into foam cells as this is presented in FIG. 2A. In the left image control $CD34^+$ cells without foam cells' formation are shown, in the right image the foam cells' formation in the presence of thrombocytes (arrow) is shown. It is demonstrated by positive immunofluorescent staining of the scavenger receptor CD68 (FIG. 2B) and transmission electromicroscopic images which show a foam cell (FIG. 2C) that the "giant cells" resulting from the co-cultivation of $CD34^+$ cells and thrombocytes are in fact foam cells.

6. Functional Characterization of the Obtained Foam Cells

To functionally characterize the foam cells which were produced in vitro it was tested whether they can absorb acetylated LDL (acLDL). This was done by an incubation of the obtained foam cells with fluorescent-labeled acLDL (Dil-AcLDL) and a staining of the dense granules with mepacrine. The subsequent confocal lasermicroscopic imaging demonstrates clearly the absorption of acLDL into the obtained foam cells and therewith their functionality; cf. FIG. 3A, scale bar 25 μm.

Moreover the method of ROS ("Reactive Oxygen Species") measurement was used. Typically in the course of an inflammation process monocytes infiltrate the vascular wall, there differentiate into macrophages and produce cytokines, proteases such as the matrix metalloproteinase (MMP) and complement factors, but also free oxidized radicals, i.e. ROS. For the foam cells resulting from the co-incubation of $CD34^+$ stem cells with thrombocytes in vitro it was detected that they release ROS and also produce matrix metalloproteinase 9 (MMP-9). This also demonstrates that functional foam cells were obtained.

Figure 3B:
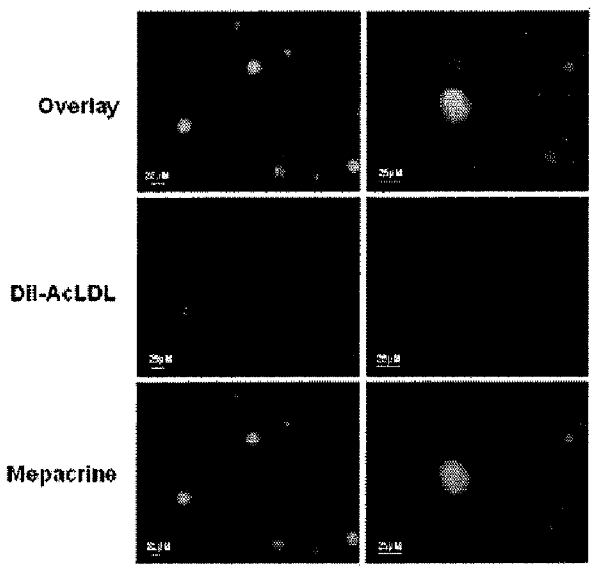
FIG. 3: (A) Absorption of acetylated LDL by foam cells; (B) inhibition of the foam cell formation by the CD68-Fc homodimer.
Figure 3B:
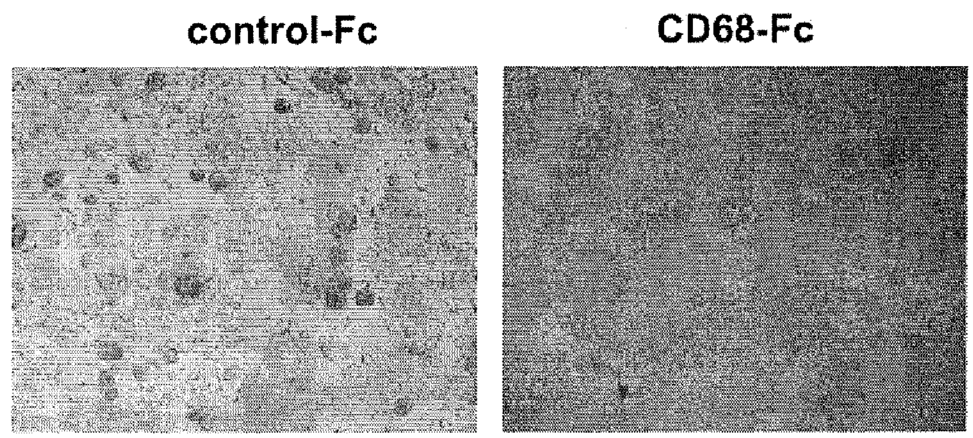

7. Inhibition of the Foam Cell Formation and Functions by the CD68-Fc Fusion Protein Foam cells were produced by co-incubation of $CD34^+$ stem cells with thrombocytes for 10 days in vitro. A portion of the cultures was treated with CD68-Fc homodimers, another portion was treated with pure Fc as a control. In the following it was microscopically analyzed whether the foam cell formation was inhibited by the incubation with the CD68-Fc homodimers. The result is shown in FIG. 3B. It is demonstrated that a treatment with Fc (left partial figure) has no effect on the foam cell formation, whereas the treatment with CD68-Fc homodimers (right partial figure) inhibited the formation of the foam cells.

Figure 3C:
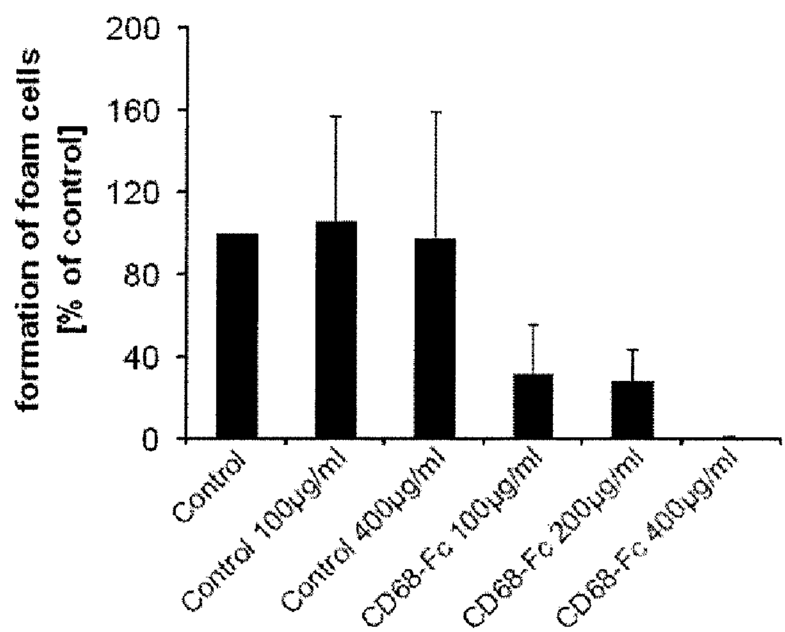

In FIG. 3C the dependence of the reduction of the foam cell formation on the dosage of the CD68-Fc homodimer is shown. At a concentration of 400 μg/ml of the CD68-Fc homodimer the foam cell formation is virtually completely inhibited. As a control again pure Fc was used.

Figure 4:
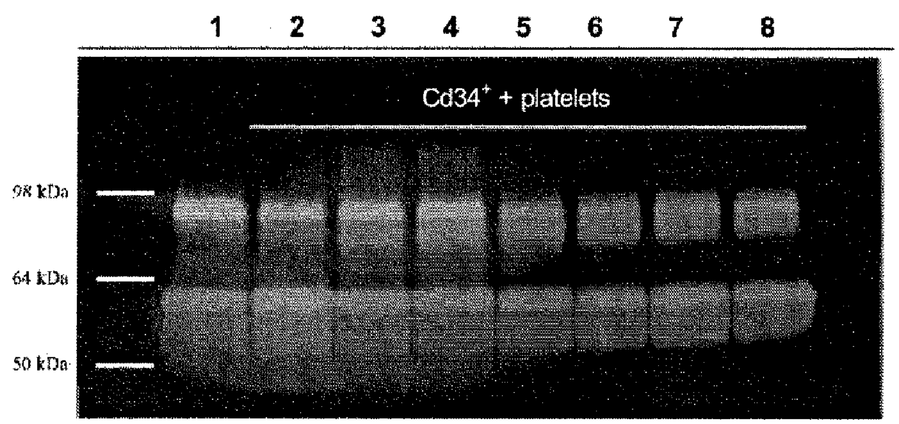
FIG. 4: Inhibition of the MMP-9 expression in the supernatant of foam cells by incubation with increasing concentrations of CD68-Fc.

Further, in another experiment it was found that the expression of MMP-9 in the supernatant of foam cells was inhibited by the incubation of increasing concentrations of CD68-Fc homodimer in relation with control protein. The result of this experiment is shown in FIG. 4. The bands correspond to the expression level of MMP-9. In the corresponding lanes the following samples were loaded: 1. control CD34, 2. control CD34, 3. control protein 100 g/ml, 4. control protein 400 μg/ml, 5. CD68-Fc homodimer 100 g/ml, 6. CD68-Fc homodimer 200 g/ml, 7. CD68-Fc homodimer 400 g/ml, 8. Fluvastatin 1 μM. It could be demonstrated that the presence of CD68-Fc homodimer (lanes 5, 6, and 7) results in a clear inhibition of the formation of MMP-9 by the foam cells similar as with the well characterized statin Fluvastatin (lane 8).

8. CD68-Fc Fusion Protein as Diagnostic Agents

Figure 5A:
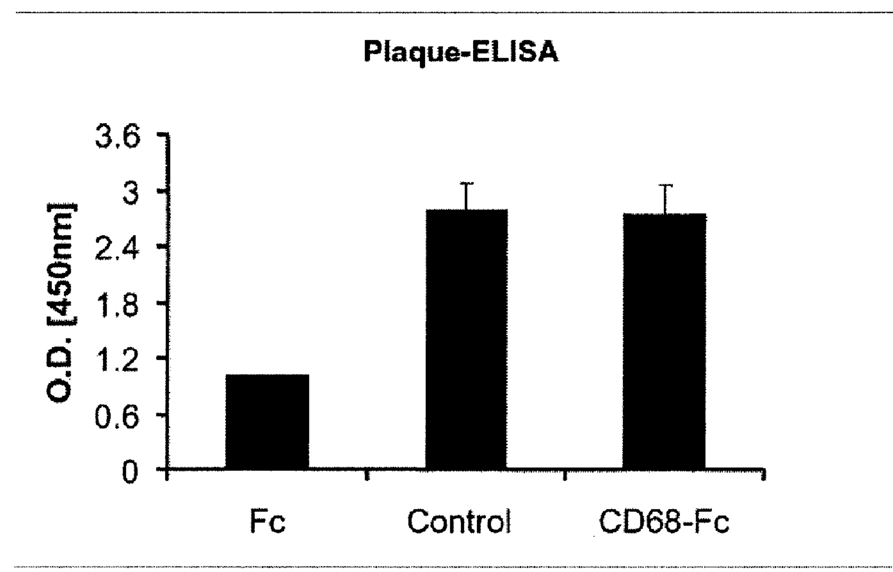
FIG. 5: Specific Fc-ELISA on atherosclerotic plaques in vitro.
Figure 5B:
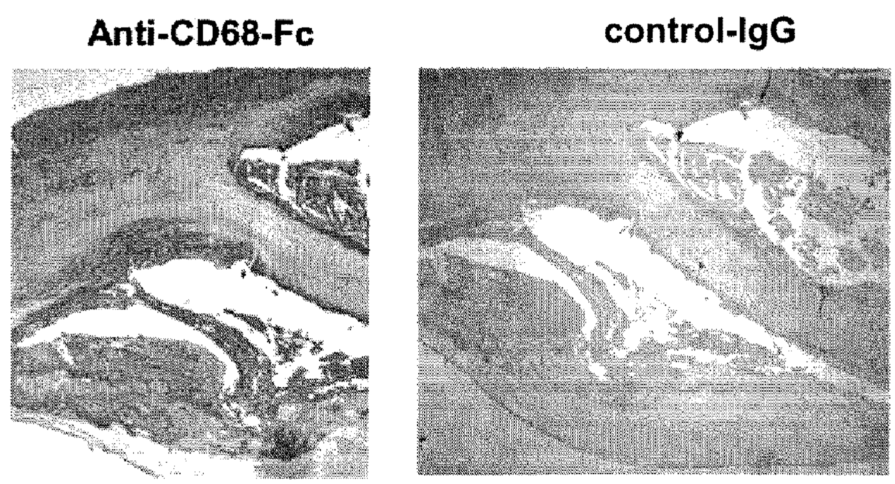

Atherosclerotic plaques from the carotid of patients, removed within the context of a surgery, were disintegrated, suspended, transferred to culture plates and surface-dried. Then a specific ELISA against the Fc portion of the CD68 or GPVI or pure Fc, respectively, was performed. The result is shown in FIG. 5A. In a parallel immunohistological analysis of human tissue from thrombus endarterectomy preparations of the Arteria carotis were performed. The result is shown in FIG. 5B.

In both cases it was shown that a significant binding of CD68-Fc fusion protein to atherosclerotic plaque tissue takes place in relation to control Fc protein (Fc) which shows no specific binding to plaque tissue. As a positive control a protein was used which binds to collagen structures in human plaque tissue (control).

Figure 6A:
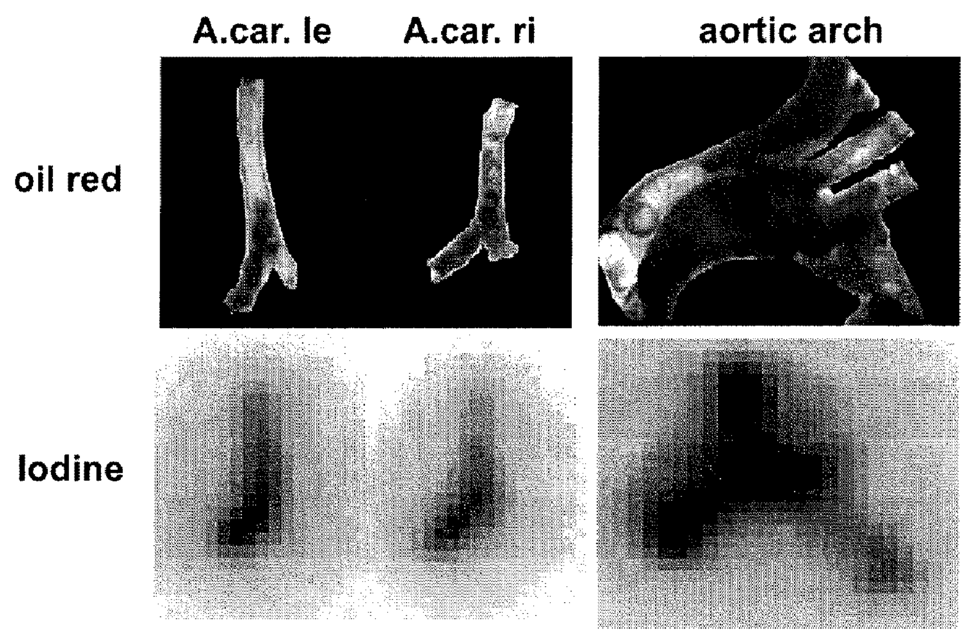
FIG. 6: In vivo application of J124-labeled CD68-Fc in atherosclerotic Apo-E-mice and in wild type mice.
Figure 6B:
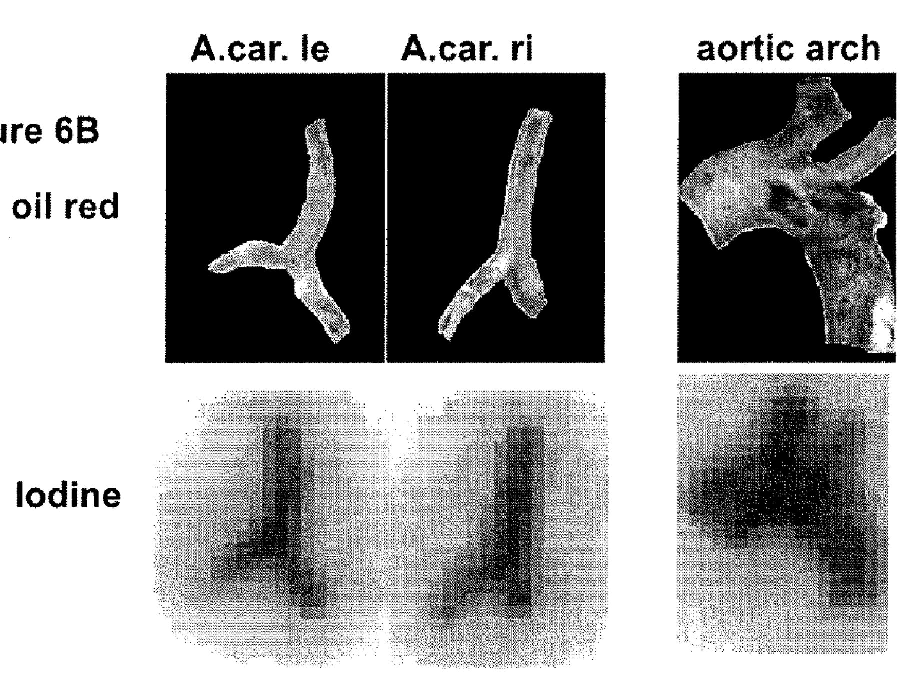
Figure 6C:
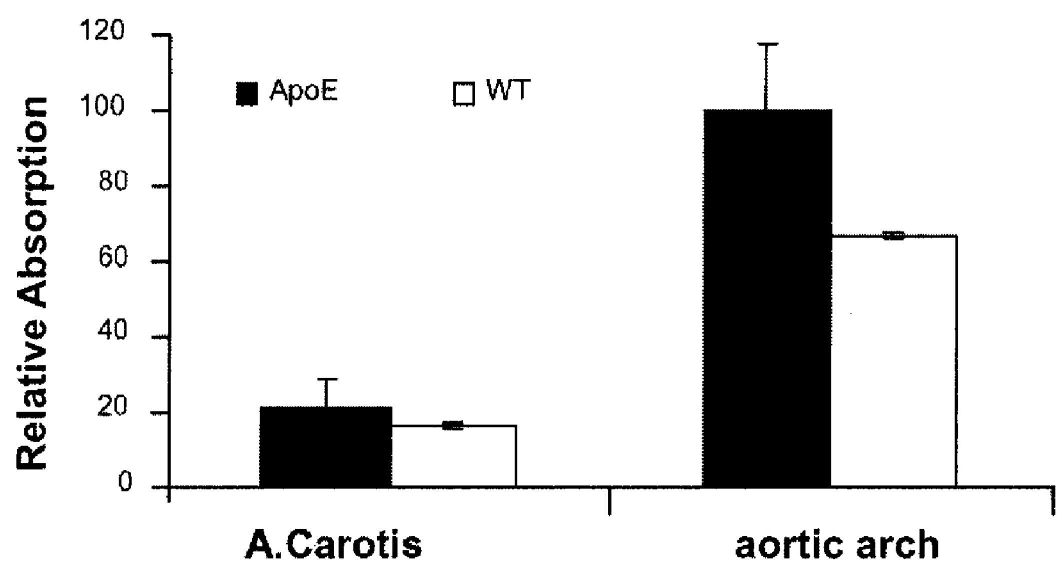

Furthermore an in vivo application of J124-labeled CD68-Fc in atherosclerotic Apo E mice and in wild type mice was performed. J124-labeled CD68-Fc was administered into 24 weeks old atherosclerotic mice or in control wild type mice without any significant atherosclerosis. The organs were then removed and the A. carotis on both sides and the aortic arch were analyzed by autoradiography ex vivo. The result is shown in FIG. 6

As shown in the partial figure (A) a remarkably increased radioactivity can be seen in the atherosclerotic vascular segments in relation to the non-atherosclerotic vessels. A staining with oil-red and a corresponding autoradiography is shown in partial figure (B). Partial figure (C) shows a quantitative evaluation of the autoradiography.

It can be shown that atherosclerotic vessels (aortic arch) removed from the Apo E mice comprise considerably increased accumulation of J124 label CD68-Fc fusion protein in relation to non-atherosclerotic vessels removed from wild type mice. No significantly increased accumulation of CD68-Fc fusion protein in Apo E mice can be seen in the area of the A. carotis in relation to the wild type.

The invention claimed is:

1. A fusion protein, comprising:

(a) a first polypeptide which specifically binds to a modified LDL, and (b) a second polypeptide which mediates a dimerization, wherein the modified LDL is oxidized LDL (oxLDL), wherein the first polypeptide comprises an amino acid sequence at least 95% identical to the sequence set forth as SEQ ID NO: 1, and wherein the second polypeptide comprises the amino acid sequence set forth as SEQ ID NO: 4.

2. The fusion protein of claim 1, wherein the first polypeptide comprises the amino acid sequence set forth as SEQ ID NO: 1, and wherein the second polypeptide comprises the amino acid sequence set forth as SEQ ID NO: 4.

3. The fusion protein of claim 2, wherein the fusion protein further comprises an element which connects said first polypeptide to said second polypeptide.

4. A method for the diagnosis of an acute or chronic vascular disease in a living being, wherein the acute or chronic vascular disease is selected from the group consisting of: atherosclerosis, atherosclerotic plaques, cardiac infarction, apoplexy, and peripheral artery occlusive disease (PAOD), the method comprising the following steps:

(1) providing the fusion protein of claim 1,
(2) introducing the fusion protein into the living being, and
(3) visualizing specific accumulation of the fusion protein in the living being by means of imaging methods.

5. A method for the diagnosis of an acute or chronic vascular disease in a living being, wherein the acute or chronic vascular disease is selected from the group consisting of: atherosclerosis, atherosclerotic plaques, cardiac infarction, apoplexy, and peripheral artery occlusive disease (PAOD), the method comprising the following steps:

(1) providing a homodimer of the fusion protein of claim 1,
(2) introducing the homodimer into the living being, and
(3) visualizing specific accumulation of the homodimer in the living being by means of imaging methods.

6. A method for the production of the fusion protein of claim 1, comprising the following steps:

(1) providing a first nucleotide sequence which encodes a first polypeptide which specifically binds to an oxLDL, wherein the first polypeptide comprises an amino acid sequence at least 95% identical to the sequence set forth as SEQ ID NO: 1,
(2) providing a second nucleotide sequence which encodes a second polypeptide which mediates the dimerization, wherein the second polypeptide comprises the amino acid sequence set forth as SEQ ID NO: 4,
(3) ligating the first and the second nucleotide sequences to obtain a fusion sequence encoding the fusion protein,
(4) cloning the fusion sequence into an expression vector,
(5) introducing the expression vector into a cell suitable for expression,
(6) expressing the fusion protein in the cell, and
(7) isolating the fusion protein from the cell.

* * * * *

UNITED STATES PATENT AND TRADEMARK OFFICE

CERTIFICATE OF CORRECTION

PATENT NO. : 8,168,160 B2
APPLICATION NO. : 12/272670
DATED : May 1, 2012
INVENTOR(S) : Gawaz and Daub It is certified that error appears in the above-identified patent and that said Letters Patent is hereby corrected as shown below:

Column 4, line 56, "necessarily has" should read -- necessarily have --.

Signed and Sealed this
Twenty-eighth Day of August, 2012

David J. Kappos
*Director of the United States Patent and Trademark Office*

CERTIFICATE OF CORRECTION

PATENT NO. : 8,168,160 B2
APPLICATION NO. : 12/272670
DATED : May 1, 2012
INVENTOR(S) : Gawaz and Daub It is certified that error appears in the above-identified patent and that said Letters Patent is hereby corrected as shown below:

On the Title page:

Item (73), "Eberhard-Karls-Universität Tübingen" should read -- Eberhard-Karls-Universitaet Tuebingen Universitaetsklinikum --.

Signed and Sealed this
Twentieth Day of November, 2012

David J. Kappos
*Director of the United States Patent and Trademark Office*